United States Patent
Ben-Zeev et al.

(10) Patent No.: US 9,255,121 B2
(45) Date of Patent: *Feb. 9, 2016

(54) ADENOSINE ANALOGS AND THEIR USE

(71) Applicant: MICRODOSE THERAPEUTX, INC., Monmouth Junction, NJ (US)

(72) Inventors: Efrat Ben-Zeev, K. Motzkin (IL); Vincent Jacques, Somerville, MA (US); Yael Marantz, Kadima (IL); A. Sekar Reddy, Burlington, MA (US); Zhaoda Zhang, Andover, MA (US); Oren Becker, Mevaseret Zion (IL); Dilara McCauley, Cambridge, MA (US); Pini Orbach, Tel Mond (IL); Sharon Shacham, Chestnut Hill, MA (US); Ashis K. Saha, Stow, MA (US); Michael Xie, Natick, MA (US)

(73) Assignee: MICRODOSE THERAPEUTX, INC., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/052,608

(22) Filed: Oct. 11, 2013

(65) Prior Publication Data

US 2014/0038912 A1    Feb. 6, 2014

Related U.S. Application Data

(63) Continuation of application No. 12/515,033, filed as application No. PCT/US2007/024150 on Nov. 16, 2007, now Pat. No. 8,569,259.

(60) Provisional application No. 60/859,919, filed on Nov. 17, 2006, provisional application No. 60/859,920, filed on Nov. 17, 2006.

(51) Int. Cl.

| | |
|---|---|
| A01N 43/04 | (2006.01) |
| A61K 31/70 | (2006.01) |
| C07H 23/00 | (2006.01) |
| C07H 19/04 | (2006.01) |
| C07H 19/20 | (2006.01) |
| C07H 15/203 | (2006.01) |
| C07H 19/16 | (2006.01) |
| C07H 21/00 | (2006.01) |
| C07H 19/10 | (2006.01) |

(52) U.S. Cl.
CPC .............. *C07H 19/20* (2013.01); *C07H 15/203* (2013.01); *C07H 19/10* (2013.01); *C07H 19/16* (2013.01); *C07H 21/00* (2013.01)

(58) Field of Classification Search
CPC ...... C07H 15/203; C07H 19/16; C07H 19/20; C07H 21/00; C07H 19/10
See application file for complete search history.

(56) References Cited

U.S. PATENT DOCUMENTS

| | | | |
|---|---|---|---|
| 5,620,676 A | 4/1997 | Jacobson et al. | 424/1.73 |
| 8,569,259 B2 * | 10/2013 | Ben-Zeev et al. | 514/45 |
| 2005/0085439 A1 | 4/2005 | Yerxa et al. | 514/50 |

FOREIGN PATENT DOCUMENTS

| | | | |
|---|---|---|---|
| WO | WO 98/18430 | 5/1998 | C07H 19/16 |
| WO | WO 03/011885 | 2/2003 | C07H 19/20 |

OTHER PUBLICATIONS

Jacobson et al., "Structure activity and molecular modeling analyses of ribose-and base-modified uridine 5'-triphosphate analogues at the human P2Y2 and P2Y4 receptors", Biochemical Pharmacology, vol. 71, No. 4, Feb. 14, 2006, (abstract only).

Bracher, et al., "Histidine 179 Mutants of GTP Cyclohydrolase I Catalyze the Formation of 2-Amino-5-formylamino-6-ribofuranosylamino-4(3H)-pyrimidinone Triphosphate", Journal of Biological Chemistry, vol. 274, No. 24, Jun. 11, 1999, pp. 16727-16735.

Sharkin, et al., "Synthesis and Substrate Properties of Modified Nucleoside 5'-Triphosphates Mimicking dATP in the Reactions of DNA Synthesis Catalyzed by DNA Polymerases", Russian Journal of Bioorganic Chemistry, vol. 27, No. 5, Sep. 10, 2001 (abstract only).

(Continued)

*Primary Examiner* — Lawrence E Crane
(74) *Attorney, Agent, or Firm* — Hayes Soloway P.C.

(57) ABSTRACT

Provided are adenosine analog compounds such as

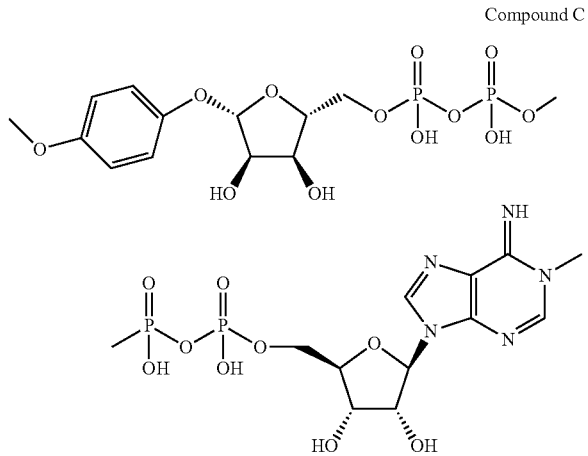

that act as P2Y receptors, e.g., the P2Y$_2$ receptor, including pharmaceutical compositions; and uses thereof to treat or prevent diseases associated with that receptor, e.g., disorders relating to mucus secretion, such as cystic fibrosis, chronic obstructive pulmonary disorder (COPD), asthma, constipation, chronic idiopathic constipation, dry mouth (xerostomia), gum disease, and gastrointestinal problems caused by radiation and chemotherapy for cancer.

16 Claims, 5 Drawing Sheets

(56) References Cited

OTHER PUBLICATIONS

Imoto, et al., "Synthesis, DNA Polymerase Incorporation, and Enzymatic Phosphate Hydrolysis of Formamidopyrimidine Nucleoside Triphosphates", Journal of the American Chemical Society, vol. 128, No. 45, Oct. 25, 2006 (abstract only).

Woenckhaus, et al., "Synthesis and biochemical properties of nicotinamide-phenyl-dinucleotide", Chemische Berichte, vol. 99, No. 5, May, 1966, pp. 1712-1717 (German only).

Nottbohm, et al., "A Colorimetric Substrate for Poly(ADP-Ribose) Polymerase-1, VPARP, and Tankyrase-1", Angew. Chem. Int. Ed. 2007, p. 2066, 2068.

International Search Report and Written Opinion issued in PCT/US07/024150, dated May 30, 2011.

International Preliminary Report on Patentability, PCT/US2007/024150, dated Jun. 16, 2011.

Official Action and translation issued in corresponding Chile patent application serial No. 3305-07 received Oct. 27, 2011.

Silverman, R.B., "The Organic Chemistry of Drug Design and Drug Action," Academic Press, Inc., San Diego, Calif., 1992, pp. 19-23 (book description only of Second Edition, 2004).

Remington et al., Remington's Pharmaceutical Sciences, $15^{th}$ Edition, pp. 1035-1038 and 1570-1580, Mack Pub. Co., 1975 (book description only).

European Office Action issued in application No. 07 867 522.0—1452, dated Jul. 2, 2015 (4 pgs).

\* cited by examiner

ADENOSINE ANALOGS AND THEIR USE

RELATED APPLICATIONS

This application is a continuation of application Ser. No. 12/515,033, filed May 15, 2009, now U.S. Pat. No. 8,569,259, issued Oct. 29, 2013, which is a national stage filing of PCT/US2007/024150, filed Nov. 16, 2007, and which claims priority to U.S. Ser. No. 60/859,919, filed on Nov. 17, 2006, and to U.S. Ser. No. 60/859,920, filed on Nov. 17, 2006, all of which are hereby incorporated by reference in their entirety.

FIELD OF THE INVENTION

The invention generally relates to the field of adenosine analog compounds that act at P2Y receptors, e.g., $P2Y_1$ or $P2Y_2$ receptor, and thus may be used for increasing mucus secretion from mucosal surfaces making them suitable for treating or preventing P2Y receptor-related diseases, e.g., disorders relating to mucus secretion, such as cystic fibrosis, chronic obstructive pulmonary disorder (COPD), dry eye, female sexual dysfunction, asthma, constipation, chronic idiopathic constipation, dry mouth (xerostomia), gum disease, and gastrointestinal problems caused by radiation and chemotherapy for cancer.

BACKGROUND OF THE INVENTION $P2Y_2$ receptors are present on body's mucosal surfaces, including the lungs, eyes, upper airways, mouth, vaginal tract and gastrointestinal tract, and on non-mucosal surfaces, such as the retinal pigment epithelium (RPE). The $P2Y_2$ receptor coordinates the entire mechanism of mucociliary clearance in the upper portion of the lower respiratory and digestive tract. This process can be regulated therapeutically by local delivery of molecules that bind to and activate these receptors.

$P2Y_2$ receptors are found on each of the three principal cell types that line the airways: ciliated epithelial cells, goblet cells, and Type II alveolar cells. Upon activation of the $P2Y_2$ receptor on ciliated epithelial cells, salt and water are released from the cell, mucous secretions are hydrated, and ciliary beat frequency is increased. Activation of the $P2Y_2$ receptor on goblet cells modulates the release of mucin. And when the $P2Y_2$ receptors on Type II alveolar cells are activated, surfactant is released, maintaining the surface tension of the smallest peripheral airways and preventing their collapse.

Activation of mucosal hydration and mucociliary clearance in the lungs and upper airways via $P2Y_2$ modulators provides opportunities for treating diseases like cystic fibrosis and upper respiratory disorders involving nasal symptoms like congestion, pressure and nasal blockage. These upper respiratory disorders include rhinosinusitis, allergic rhinitis, and upper respiratory infections like the common cold and influenza. Also, increasing mucociliary clearance in the lungs allows for non-invasive collection of mucus samples from the lungs, which may be beneficial in the diagnosis of lung cancer.

Chronic obstructive pulmonary disease (COPD) is characterized by mucus secretion retention in the lungs, resulting in progressive lung dysfunction over time. Many patients diagnosed with COPD have a disorder called chronic bronchitis (CB). Cystic fibrosis and Primary Ciliary Dyskinesia (PCD) are other examples of lung disorders that have a clinical profile similar to COPD. Primary or secondary ciliary dyskinesia results in retained secretions that can only be cleared by coughing. Most patients with COPD utilize coughing to help clear retained secretions because of impaired mucociliary clearance.

Sinusitis, also characterized by an accumulation of retained mucous secretions, is an inflammation of the paranasal sinuses typically associated with an upper respiratory infection. This condition affects many people in the US.

Otitis media (OM) is a viral or bacterial infection of the middle ear, primarily afflicting children under the age of three. It is usually precipitated by an upper respiratory infection that spreads into the middle ear via the nasopharynx and eustachian tube. Following antibiotic treatment, accumulated fluid in the middle ear causes hearing impairment and potential language and cognitive development delays. Improved clearing of middle ear secretions would reduce or eliminate significant sequelae of otitis media.

Pneumonia is an illness of the respiratory system that is linked to retained secretions. This illness afflicts many people each year and is a leading cause of death for chronically ill patients. Amongst those at risk for developing pneumonia, patients that are immobilized generally have a high risk of developing the illness.

At times, it is therapeutically desirable to increase drainage of the lacrimal system because improper functioning of the lacrimal drainage system can result in excessive tearing (epiphora), mucopurulent discharge, and/or recurrent dacryocystitis. Current treatments for nasolacrimal duct obstruction are mostly invasive surgical procedures, which are not desirable. Tear secretion can be stimulated from lacrimal accessory tissues via $P2Y_2$ and/or $P2Y_4$ purinergic receptor-mediated mechanisms similar to those which hydrate airway epithelia. Dry eye disease is the general term for indications produced by abnormalities of the precorneal tear film characterized by a decrease in tear production or an increase in tear film evaporation, together with the ocular surface disease that results. The current pharmaceutical treatment of dry eye disease is often limited to administration of artificial tears (saline solution) to temporarily rehydrate the eyes. This treatment generally provides only short-term relief, and frequent dosing is necessary.

Normally, mucous secretions are removed via the mucociliary clearance (MCC) system. MCC relies on the integrated action of three components: 1) mucus secretion by goblet cells and submucosal glands; 2) the movement of cilia on epithelial cells which propels the mucus across the luminal surface; and 3) ion transport into and out of luminal epithelial cells which concomitantly controls the flow of water into the mucus. Secretory functions of the uterine, cervical and vaginal mucous cells also have a profound impact on the function and health of the reproductive tract. For example, the quality and quantity of cervical mucus changes throughout the menstrual cycle and such changes dramatically influence fertility. Under the influence of rising estrogen levels, cervical mucus becomes thin, allowing the passage of spermatozoa. Later in the menstrual cycle, as progesterone levels increase, mucus becomes thick and hostile to sperm penetration, thereby closing the window of fertility. Such thickening of cervical mucus is thought to be one of the primary modes of contraceptive action for progestin-only contraceptives.

Estrogen stimulates the production of thin, isotonic mucus, with increased amounts of high molecular weight glycoproteins. Cervical mucus contains 98% water at mid cycle and 90% at other times. Cervical mucus is also rich in metallic ions, enzymes (such as alkaline phosphatase, etc.), soluble proteins, and salts. The gel phase of cervical mucus contains high molecular weight glycoproteins called mucin. Mucin micelles cross-link by disulfide bridges. Estrogen and progesterone control the arrangement of these micelles.

Postmenopausal women often experience atrophic vaginitis or vaginal dryness. During vaginal atrophy, the vaginal epithelium decreases in thickness, hydration, ruggae (folds), and blood flow. Causes of atrophic vaginitis include a decrease in the amount of estrogen present both locally and systemically as well as environmental factors such as chemotherapy, antihistamines, smoking cigarettes, excessive exercise, and vaginal products (i.e. douches, deodorants, and perfumes).

Estrogens or hormone replacement therapies can be effective in reducing vaginal dryness, but possible dangerous side effects include higher incidences of breast cancer, endometrial cancer, blood clots, nausea, breast tenderness, and headache. Products that are available over-the-counter include lubricants as moisturizers. These products are mostly water, provide only temporary relief for symptoms, and have virtually no long-term benefits to the vaginal tissue.

Accordingly, the need exists for compounds that act at P2Y receptors, e.g., $P2Y_1$ or $P2Y_2$ receptor, and thereby provide a therapeutic benefit by increasing mucus secretion from mucosal surfaces.

SUMMARY OF THE INVENTION

The present invention provides new compositions and methods for modulating mucus production at mucosal surfaces, e.g., of the lungs, throat, sinuses, nasal passages, ear canals, eyes and female reproductive tract. In an embodiment, the invention provides adenosine analog compounds that act at P2Y receptors, and their use as medicinal agents. More particularly, the invention provides adenosine analog compounds and their use as modulators of P2Y receptors, e.g., $P2Y_2$. The invention further provides novel compounds and medical methods of treatment of diseases associated with P2Y receptors, e.g., disorders relating to mucus secretion, such as cystic fibrosis, chronic obstructive pulmonary disorder (COPD), asthma, constipation, chronic idiopathic constipation, dry mouth (xerostomia), gum disease, and gastrointestinal problems caused by radiation and chemotherapy for cancer.

One aspect of the invention provides a compound of Formula I:

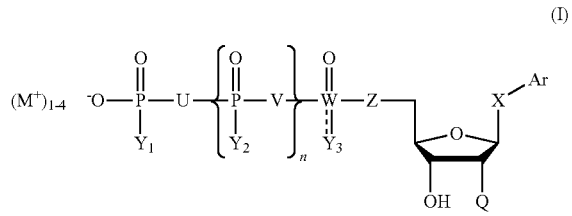

(I)

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof, wherein:

Ar is selected from the group consisting of a substituted or unsubstituted aryl, alkyl, cycloalkyl, arylalkyl, or a heteroaryl or fused heteroaryl group containing 1-3 heteroatoms such as O, S and N, wherein the Ar moiety is optionally substituted with one or more of halo, hydroxy, alkyl, alkoxy, carboxy, cyano, nitro, sulfonamido, sulfonate, amino, alkylamino or di-alkylamino; provided that when X is O, Ar is neither unsubstituted phenyl, anilino, nor 4-nitrophenyl;

X is selected from the group consisting of O, N, S, S(O), $S(O_2)$, N(R'), —C(O)N(R')—, and —$(CH_2)_m X^1$—;

$X^1$ is O, S, S(O), $S(O_2)$, or N(R');

R' is H, alkyl, or aralkyl;

Q is selected from the group consisting of H; OH; lower alkoxy; halo; mono-, di- or trihalomethyl; amino; lower alkylamino; and lower dialkylamino;

U and V are independently selected from the group consisting of O; NH; lower alkylamino diradical; lower dialkylamino diradical; methylene; and mono- or dihalomethylene;

$Y_1$, $Y_2$, and $Y_3$ are independently O, O$^-$; S$^-$; or substituted or unsubstituted lower alkoxy, aryloxy, aralkyloxy, or cycloalkyloxy;

Z is selected from the group consisting of O; NH; lower alkylamino diradical; and lower dialkylamino diradical;

m and n are independently 0, 1 or 2;

W is P or S, provided that when n is W is S, $Y_3$ is O; and M is H or a salt-forming cation, such as Na$^+$, K$^+$, or $NH_4^+$.

Another aspect of the invention provides a compound of Formula IA:

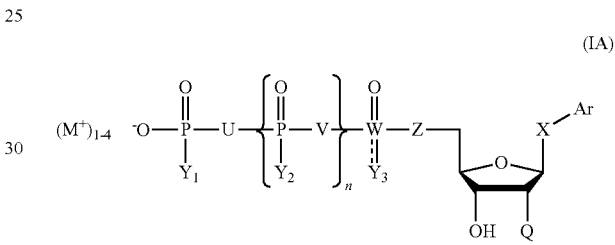

(IA)

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof, wherein:

Ar is aryl, alkyl, cycloalkyl, aralkyl, or a heteroaryl or fused heteroaryl group containing 1-4 heteroatoms such as O, S or N; each of which is optionally substituted with one or more of halo, hydroxy, alkyl, alkoxy, carboxy, cyano, nitro, sulfonamido, sulfonate, amino, imino, alkylamino, or di-alkylamino; provided that when X is O, Ar is neither unsubstituted phenyl, anilino, nor 4-nitrophenyl;

X is a bond or is selected from the group consisting of O, N, S, S(O), $S(O_2)$, N(R'), —C(O)N(R')—, and —$(CH_2)_m X^1$—;

$X^1$ is O, S, S(O), $S(O_2)$, or N(R');

R' is H, alkyl, or aralkyl;

Q is selected from the group consisting of H; OH; lower alkoxy; halo; mono-, di- or trihalomethyl; amino; lower alkylamino; and lower dialkylamino;

U and V each represent independently for each occurrence O; NH; a lower alkylamino diradical; methylene; or mono- or dihalomethylene;

$Y_1$, $Y_2$, and $Y_3$ each represent independently for each occurrence O, O$^-$; S$^-$; or substituted or unsubstituted lower alkoxy, aryloxy, aralkyloxy, or cycloalkyloxy;

Z is O, NH, or a lower alkylamino diradical;

m and n are independently 0, 1 or 2;

W is P or S, provided that when W is S, $Y_3$ is O; and M is H or a salt-forming cation (such as Na$^+$, K$^+$, or $NH_4^+$).

Another aspect of the invention provides a compound of Formula IIA:

(IIA)

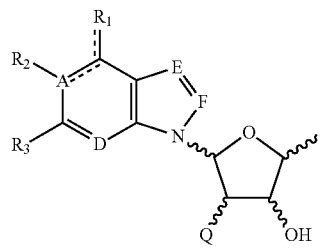 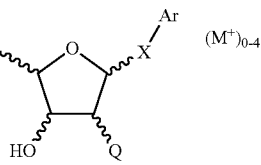

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof, wherein:

A, D, and E are independently N, $C(R_5)$, or CH;

F is N or $C(R_4)$;

$R_1$ is H, oxo, lower alkoxy, lower alkylamino, lower dialkylamino, imino, lower alkyl-substituted imino, lower thioalkyl, aryl, substituted or unsubstituted lower alkyl, or lower alkyl-substituted aryl;

$R_2$ is absent or is selected from the group consisting of lower alkyl, lower alkoxy, lower alkyl-substituted aryl, aralkyl, and cycloalkyl;

$R_3$ and $R_4$ are independently H, lower thioalkyl, substituted lower alkyl, or unsubstituted lower alkyl;

$R_5$ is lower alkyl, lower alkoxy, lower alkyl-substituted aryl, aralkyl, or cycloalkyl;

Ar is aryl, alkyl, cycloalkyl, arylalkyl, or a heteroaryl or fused heteroaryl group containing 1-4 heteroatoms such as O, S or N; each of which is optionally substituted with one or more of halo, hydroxy, alkyl, alkoxy, carboxy, cyano, nitro, sulfonamido, sulfonate, amino, alkylamino, or di-alkylamino; provided that when X is O, Ar is neither unsubstituted phenyl, anilino, nor 4-nitrophenyl;

X is a bond or is selected from the group consisting of O, N, S, S(O), S(O$_2$), N(R'), —C(O)N(R')—, and —(CH$_2$)$_m$—X$^1$—;

$X^1$ is O, S, S(O), S(O$_2$), or N(R');

R' is H, alkyl, or aralkyl;

Q represents independently for each occurrence H; OH; lower alkoxy; halo; mono-, di- or trihalomethyl; amino; lower alkylamino; or lower dialkylamino;

U and V each represent independently for each occurrence O; NH; a lower alkylamino diradical; methylene; or mono- or dihalomethylene;

$Y_2$ and $Y_3$ each represent independently for each occurrence O, O$^-$; S$^-$; or substituted or unsubstituted lower alkoxy, aryloxy, aralkyloxy, or cycloalkyloxy;

M is H or a salt-forming cation (such as Na$^+$, K$^+$, or NH$_4^+$);

Z represents independently for each occurrence O, NH, or a lower alkylamino diradical;

m and n are independently 0, 1 or 2; and

W is P or S, provided that when W is S, $Y_3$ is O.

Another aspect of the invention provides a compound of Formula IIB:

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof, wherein:

Ar is aryl, alkyl, cycloalkyl, arylalkyl, or a heteroaryl or fused heteroaryl group containing 1-4 heteroatoms such as O, S or N; each of which is optionally substituted with one or more of halo, hydroxy, alkyl, alkoxy, carboxy, cyano, nitro, sulfonamido, sulfonate, amino, alkylamino, or di-alkylamino; provided that when X is O, Ar is neither unsubstituted phenyl, anilino, nor 4-nitrophenyl;

X is a bond or is selected from the group consisting of O, N, S, S(O), S(O$_2$), N(R'), —C(O)N(R')—, and —(CH$_2$)$_m$—X$^1$—;

$X^1$ is O, S, S(O), S(O$_2$), or N(R');

R' is H, alkyl, or aralkyl;

Q represents independently for each occurrence H; OH; lower alkoxy; halo; mono-, di- or trihalomethyl; amino; lower alkylamino; or lower dialkylamino;

U and V each represent independently for each occurrence O; NH; a lower alkylamino diradical; a lower dialkylamino diradical; methylene; or mono- or dihalomethylene;

$Y_1$ is CH$_2$ or NH;

$Y_2$ and $Y_3$ each represent independently for each occurrence O, O$^-$; S$^-$; or substituted or unsubstituted lower alkoxy, aryloxy, aralkyloxy, or cycloalkyloxy;

M is H or a salt-forming cation (such as Na$^+$, K$^+$, or NH$_4^+$);

Z represents independently for each occurrence O, NH, or a lower alkylamino diradical;

m and n are independently 0, 1 or 2;

W is P or S, provided that when W is S, $Y_3$ is O.

(IIB)

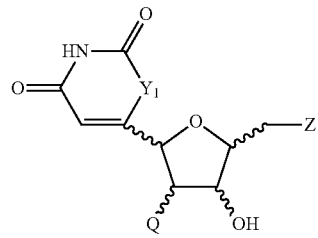 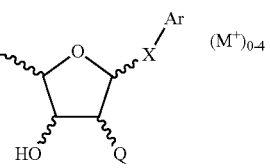

Another aspect of the invention provides a compound of Formula IIIA:

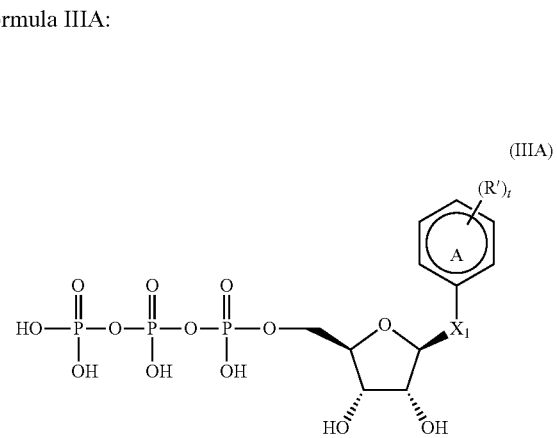
(IIIA)

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof, wherein:

is phenyl or pyridyl;

$X_1$ is O, NH, N(alkyl), —N(alkyl)-C(O)—, —C(O)N(alkyl)-, —N(alkyl)-CH$_2$—, —CH$_2$—N(alkyl)-, —CH$_2$N(alkyl)-C(O)—, or —C(O)N(alkyl)-CH$_2$—;

R' represents independently for each occurrence halo, hydroxy, alkyl, alkoxy, carboxy, cyano, nitro, sulfonamido, sulfonate, amino, alkylamino, or di-alkylamino; and t is 0, 1, 2, or 3.

Another aspect of the invention provides a compound of Formula IIIB:

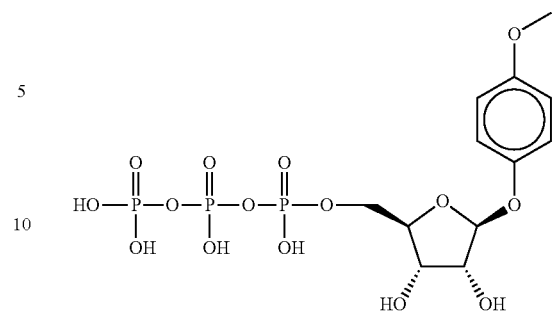
(IIIB)

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof.

Another aspect of the invention provides a compound of Formula IV:

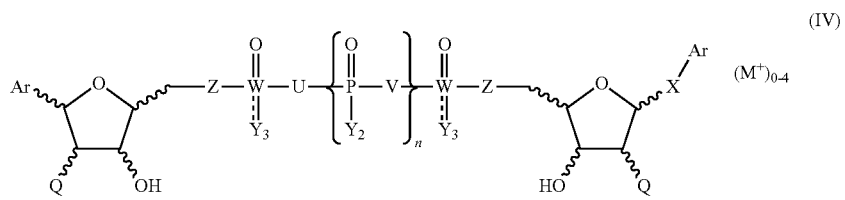
(IV)

including enantiomers, diastereomers, enantiomerically enriched mixtures, racemic mixtures, prodrugs, crystalline forms, non-crystalline forms, amorphous forms, solvates, metabolites, and pharmaceutically acceptable salts thereof, wherein:

Ar is aryl, alkyl, cycloalkyl, aralkyl, or a heteroaryl or fused heteroaryl group containing 1-4 heteroatoms such as O, S or N; each of which is optionally substituted with one or more of halo, hydroxy, alkyl, alkoxy, carboxy, cyano, nitro, sulfonamido, sulfonate, amino, alkylamino, or di-alkylamino; provided that when X is O, Ar is neither unsubstituted phenyl, anilino, nor 4-nitrophenyl;

X is O, N, S, S(O), S(O$_2$), N(R'), —C(O)N(R')—, or —(CH$_2$)$_m$X$^1$—;

$X^1$ is O, S, S(O), S(O$_2$), or N(R');

R' is H, alkyl, or aralkyl;

Q represents independently for each occurrence H; OH; lower alkoxy; halo; mono-, di- or trihalomethyl; amino; lower alkylamino; or lower dialkylamino;

U and V each represent independently for each occurrence O; NH; a lower alkylamino diradical; a lower dialkylamino diradical; methylene; or mono- or dihalomethylene;

$Y_2$ and $Y_3$ each represent independently for each occurrence O, O$^-$; S$^-$; or substituted or unsubstituted lower alkoxy, aryloxy, aralkyloxy, or cycloalkyloxy;

M is H or a salt-forming cation (such as Na$^+$, K$^+$, or NH$_4^+$);

Z represents independently for each occurrence O, NH, or a lower alkylamino diradical;

m and n are independently 0, 1 or 2; and

W is P or S, provided that when W is S, $Y_3$ is O.

In certain embodiments, the compound is one of the following:

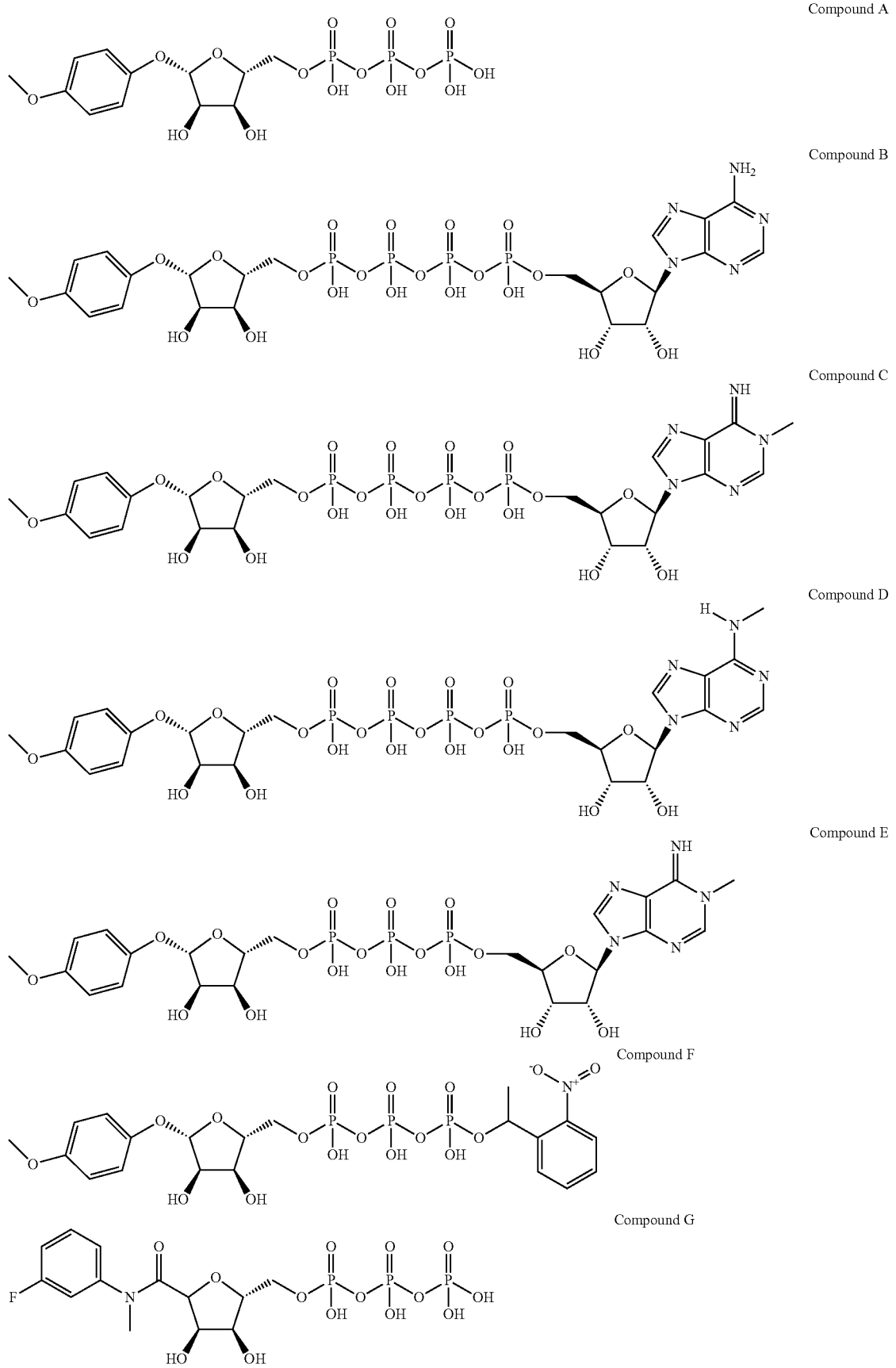

Compound H
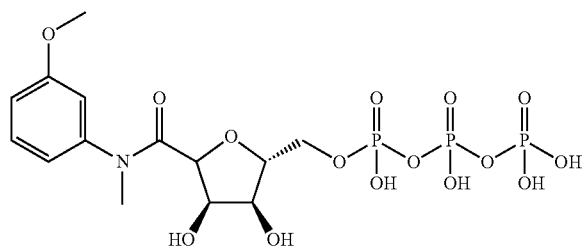
Compound J
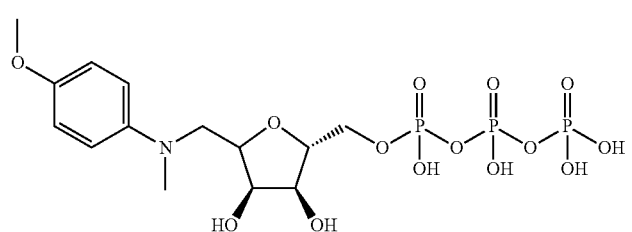
Compound K
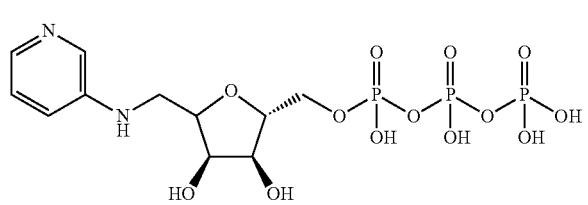
Compound M
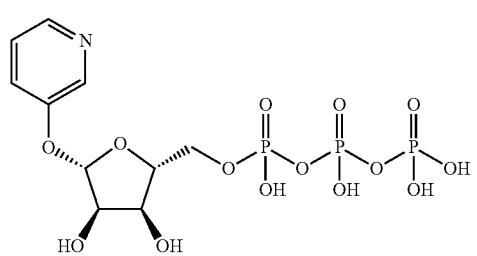
Compound N
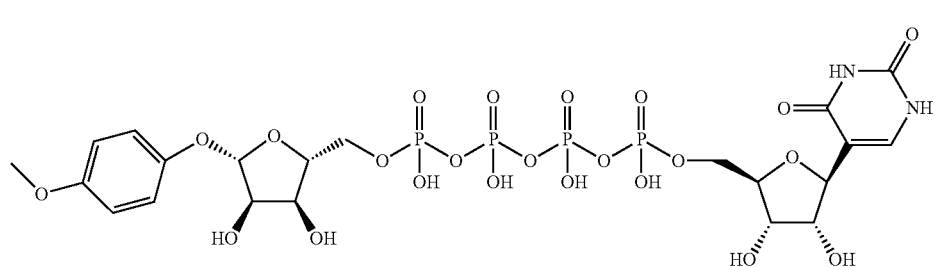
Compound P
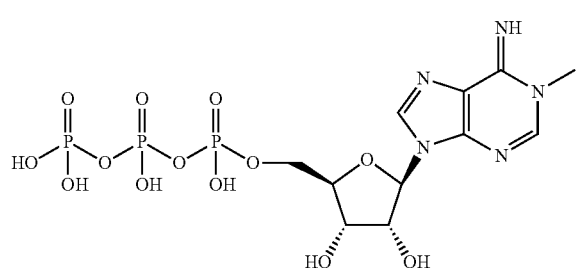

Another aspect of the invention provides pharmaceutical compositions comprising a compound of one of the above formulae admixed with a pharmaceutically acceptable carrier or excipient.

Another aspect of the invention provides the use a compound or composition described herein in the prevention or treatment of diseases in which P2Y receptors are involved.

Another aspect of the invention provides compositions comprising one or more compounds described herein, and a pharmaceutically acceptable carrier.

Another aspect of the invention provides a method of treating various conditions, such as cystic fibrosis, sinusitis, otitis media, ventilator associated pneumonia, chronic bronchitis, chronic obstructive pulmonary disorder, primary ciliary dyskinesia, asthma, bronchiectasis, post-operative atelectasis, Kartagener's syndrome, constipation, chronic idiopathic constipation, dry mouth (xerostomia), mouth ulcer, gum disease, mycositis, gastro-esophageal reflux disease, peptic ulcer, heartburn, esophagitis, Sjorgen's syndrome, inflammatory bowel disease, gastrointestinal problems caused by radiation and chemotherapy for cancer by administering to a subject in need thereof a therapeutically effective amount a compound described herein. In certain embodiments, the compound is administered in the form of a pharmaceutical composition comprising the compound in an admixture with a pharmaceutically acceptable excipient, diluent, or carrier.

Another aspect of the invention provides a method of treating constipation comprising administering to a subject in need thereof a therapeutically effective amount of a compound described herein.

In certain embodiments, the subject is a human.

Another aspect of the invention provides a method of treating a disease associated with expression or activity of a P2Y receptor in a patient, comprising administering to the patient a therapeutically effective amount of a compound described herein.

Another aspect of the invention provides methods of modulating the activity of a P2Y receptor comprising exposing said receptor to a compound described herein.

Another aspect of the invention provides compounds of the above formulae for use in therapy.

Another aspect of the invention provides use of a compound of the above formulae for the manufacture of a medicament for treating a disease associated with the expression or activity of a P2Y receptor.

DETAILED DESCRIPTION OF THE INVENTION

Figure 1:
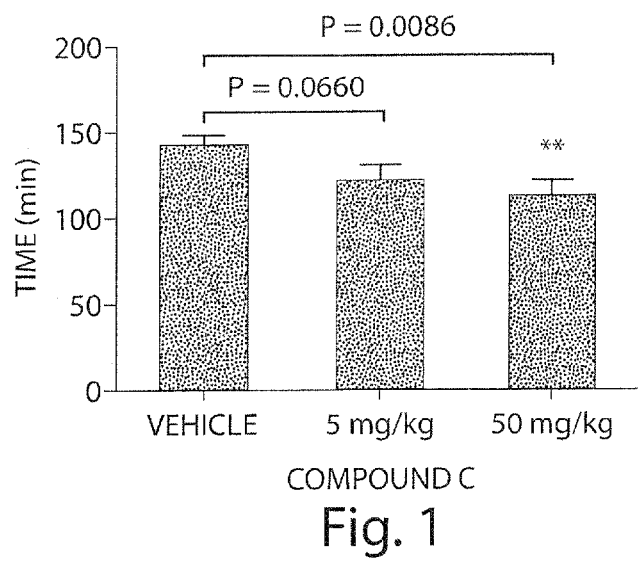
FIG. 1 depicts the results of an assay measuring the total gastrointestinal transit time (in minutes) in male Balb/C mice. The graph illustrates the time to first red-colored feces as a function of the dose of compound C (N=18 mice for vehicle, 7 for 5 mg/kg, and 8 for 50 mg/kg).

The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified. If a variable is presented without an accompanying definition, then the previous definition of the variable controls.

DEFINITIONS

For convenience, certain terms used in the specification, examples, and appended claims are collected here.

"P2Y receptor modulator" or "P2Y modulator" includes compounds having effect at the P2Y receptors, e.g., $P2Y_1$, P2Y$_2$, P2Y$_4$ or P2Y$_6$, particularly compounds having a modulating effect (increase or decrease) primarily at P2Y$_2$.

"Treating", includes any effect, e.g., lessening, reducing, modulating, or eliminating, that results in the improvement of the condition, disease, disorder, etc.

The symbol "⌇⌇⌇" indicates a point of attachment.

The symbol "===" indicates that the bond may be either a single bond or double bond.

"Alkyl" includes saturated aliphatic groups, e.g., straight-chain alkyl groups such as methyl, ethyl, propyl, butyl, pentyl, hexyl, heptyl, octyl, nonyl, and decyl; branched-chain alkyl groups (e.g., isopropyl, tert-butyl, and isobutyl); cycloalkyl (alicyclic) groups like cyclopropyl, cyclopentyl, cyclohexyl, cycloheptyl, and cyclooctyl); lower alkyl-substituted cycloalkyl groups; and cycloalkyl-substituted alkyl groups. In an embodiment, alicyclic rings do not include bridged rings.

"Alkyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkyl groups may have six or fewer carbon atoms in their backbone (e.g., $C_1$-$C_6$ for straight chain, $C_3$-$C_6$ for branched chain), and more preferably four or fewer. Preferred cycloalkyl groups have from three to eight carbon atoms in their ring structure, and more preferably five or six carbons in the ring structure. "$C_1$-$C_6$" includes alkyl groups containing one to six carbon atoms.

"Substituted alkyls" refers to alkyl moieties having substituents replacing a hydrogen on one or more carbons of the hydrocarbon backbone. Such substituents can include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, thiocarboxylate, sulfates, alkylsulfinyl, sulfonato, sulfamoyl, sulfonamido, nitro, trifluoromethyl, cyano, azido, or heterocyclyl.

The term "aryl" is art-recognized and includes 5-, 6- and 7-membered single-ring aromatic groups that may include from zero to four heteroatoms, as well as conjugated (i.e., multicyclic) systems having at least one ring that is aromatic. Examples of aryl groups include benzene, phenyl, tolyl and the like. Multicyclic aryl groups include tricyclic and bicyclic systems, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indolizine, tetralin, and methylenedioxyphenyl. The aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

Aryl groups having heteroatoms in the ring structure may also be referred to as "aryl heterocycles", "heterocycles," "heteroaryls" or "heteroaromatics"; e.g., pyrrole, furan, thiophene, thiazole, isothiazole, imidazole, triazole, tetrazole, pyrazole, oxazole, isooxazole, pyridine, pyrazine, pyridazine, and pyrimidine. The aromatic ring can be substituted at one or more ring positions with, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "alkylaryl" or an "aralkyl" moiety is an alkyl substituted with an aryl group (e.g., phenylmethyl (benzyl)).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, and decenyl), branched-chain alkenyl groups, cycloalkenyl groups such as cyclopropenyl, cyclopentenyl, cyclohexenyl, cycloheptenyl, and cyclooctenyl; alkyl or alkenyl-substituted cycloalkenyl groups, and cycloalkyl or cycloalkenyl-substituted alkenyl groups.

"Alkenyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound.

Straight or branched alkenyl groups may have six or fewer carbon atoms in their backbone (e.g., $C_2$-$C_6$ for straight chain, $C_3$-$C_6$ for branched chain.) Preferred cycloalkenyl groups have from three to eight carbon atoms in their ring structure, and more preferably have five or six carbons in the ring structure. The term "$C_2$-$C_6$" includes alkenyl groups containing two to six carbon atoms.

"Substituted alkenyls" refers to alkenyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups.

"Alkynyl" groups may also optionally include heteroatoms, i.e., where oxygen, nitrogen, sulfur or phosphorous atoms replaces one or more hydrocarbon backbone carbon atoms, particularly where the substitution does not adversely impact the efficacy of the resulting compound Straight or branched chain alkynyls group may have six or fewer carbon atoms in their backbone (e.g., $C_2$-$C_6$ for straight chain, $C_3$-$C_6$ for branched chain). The term "$C_2$-$C_6$" includes alkynyl groups containing two to six carbon atoms.

"Substituted alkynyls" refers to alkynyl moieties having substituents replacing a hydrogen on one or more hydrocarbon backbone carbon atoms. Such substituents can include alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have corresponding chain lengths, e.g., 2-5 carbon atoms.

"Acyl" includes compounds and moieties which contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "oxo" refers to a "O=" substituent. For example, a cyclohexanone is a cyclohexane bearing an oxo group.

"Acylamino" includes moieties wherein an acyl moiety is bonded to an amino group. For example, the term includes alkylcarbonylamino, arylcarbonylamino, carbamoyl and ureido groups. "Alkylamino" includes moieties wherein an alkyl moiety is bonded to an amino group; "dialkylamino", "arylamino", "diarylamino", and "alkylarylamino" are analogously named.

"Alkoxyalkyl" includes moieties where an alkoxy group is bonded to an alkyl group; "alkoxyaryl", "thioalkoxyalkyl", "alkylaminoalkyl" and "alkylthioalkyl" are analogously named.

"Alkoxy" includes alkyl, alkenyl, and alkynyl groups covalently linked to an oxygen atom. Examples of alkoxy groups include methoxy, ethoxy, isopropyloxy, propoxy, butoxy, and pentoxy groups. Examples of "substituted alkoxy" groups include halogenated alkoxy groups. Substituted alkoxy groups can include alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl substituents. Examples of halogen-substituted alkoxy groups include fluoromethoxy, difluoromethoxy, trifluoromethoxy, chloromethoxy, dichloromethoxy, and trichloromethoxy. In a preferred embodiment, the "alkoxy" group is an alkyl group covalently linked to an oxygen atom.

The terms "heterocyclyl" or "heterocyclic group" include closed ring structures, e.g., 3- to 10-, or 4- to 7-membered rings which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like.

Heterocyclic rings may be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkyl carbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In an embodiment, heterocyclic rings do not include bridged rings.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" is art recognized and refers to —OH.

The term "halogen" includes fluorine, bromine, chlorine, iodine, etc. The term "perhalogenated" generally refers to a moiety wherein all hydrogens are replaced by halogen atoms.

The terms "amine" and "amino" are art-recognized and refer to both unsubstituted and substituted amines, e.g., a moiety that may be represented by the general formulas:

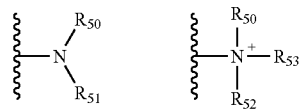

wherein $R_{50}$, $R_{51}$ and $R_{52}$ each independently represent a hydrogen, an alkyl, an alkenyl, —$(CH_2)_m$—$R_{61}$, or $R_{50}$ and $R_{51}$, taken together with the N atom to which they are attached complete a heterocycle having from 4 to 8 atoms in the ring structure; $R_{61}$ represents an aryl, a cycloalkyl, a cycloalkenyl, a heterocycle or a polycycle; and m is zero or an integer in the range of 1 to 8.

The term "imino" is art-recognized and may be represented by the general formula:

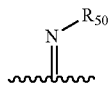

wherein $R_{50}$ is H, alkyl, aryl, or aralkyl.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Contacting" refers to the bringing together of indicated moieties in an in vitro or in vivo system. For example, "contacting" a P2Y receptor with a compound described herein includes the administration of the compound to an individual or patient, such as a human, having a P2Y receptor, as well as, for example, introducing a compound into a sample containing a cellular or purified preparation containing the P2Y receptor.

"Selective" means that a compound binds to or inhibits a certain P2Y receptor with greater affinity or potency, respectively, compared to at least one other receptors, or preferably compared to all other receptors of the same class (e.g., all the P2Y receptors). In some embodiments, the compounds of the invention have binding or inhibition selectivity for $P2Y_2$ over any other P2Y receptor. Selectivity can be at least about 10-fold, at least about 20-fold, at least about 50-fold, at least about 100-fold, at least about 200-fold, at least about 500-fold or at least about 1000-fold. Binding affinity and inhibitor potency can be measured according to routine methods in the art.

An "anionic group," as used herein, refers to a group that is negatively charged at physiological pH. Preferred anionic groups include carboxylate, sulfate, sulfonate, sulfonate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp. 19-23).

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

As indicated above, the invention provides a compound of formula IA:

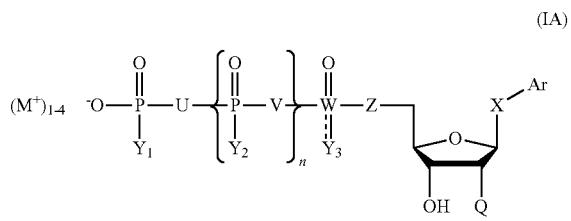

(IA)

A specific value for Ar is phenyl. Another specific value for Ar is pyridyl. Another specific value for Ar is

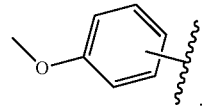

Another specific value for Ar is

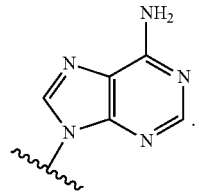 [SMILES: *n1cnc2c(N)ncnc21]

Another specific value for Ar is

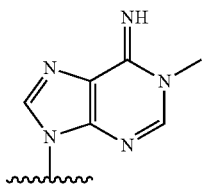

Another specific value for Ar is

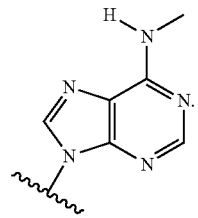 [SMILES: *n1cnc2c(NC)ncnc21]

Another specific value for Ar is

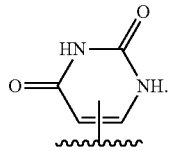

The Ar group can be optionally substituted with up to 3 groups, each independently selected from halo, hydroxy, alkyl, alkoxy, carboxy, cyano, nitro, sulfonamido, sulfonate, amino, imino, alkylamino and di-alkylamino; provided that when X is O, Ar is neither unsubstituted phenyl, anilino, nor 4-nitrophenyl.

A specific value for X is a bond. Another specific value for X is O.

Other specific values for X include N, S, S(O), S(O$_2$), N(R'), —C(O)N(R')—, or —(CH$_2$)$_m$X$^1$—; wherein X$^1$ is O, S, S(O), S(O$_2$), or N(R'); R' is H, alkyl, or aralkyl; and m is 0, 1, 2, or 3.

A specific value for Q is H. Another specific value for Q is OH. Other specific values for Q include methoxy, ethoxy, fluoro, chloro, trifluoromethyl, NH$_2$, N(H)Me, N(H)Et, (Me)$_2$N, or (Et)$_2$N.

A specific value for U is O. Another specific value for U is NH. Another specific value for U is methyl amino diradical. Another specific value for U is an ethyl amino diradical.

A specific value for V is O. Another specific value for V is NH. Another specific value for V is a methyl amino diradical. Another specific value for V is an ethyl amino diradical.

Specific values for Y$_1$, Y$_2$, and Y$_3$ are O$^-$ and S$^-$. Other specific values for Y$_1$, Y$_2$, and Y$_3$ include substituted or unsubstituted methoxy, ethoxy, trifluoromethoxy, phenoxy, benzyloxy, or cyclopropyl-, butyl-, pentyl- or hexyloxy, any of which may be optionally substituted.

A specific value for Z is O. Another specific value for Z is NH. Another specific value for Z is methylamino diradical.

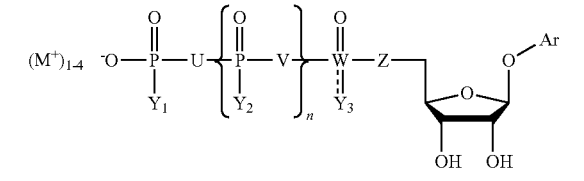

A specific group of compounds of formula IA are compounds of formula IA-2

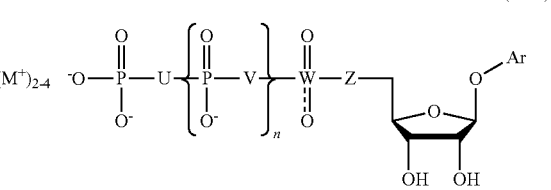

A specific group of compounds of formula IA are compounds of formula IA-3

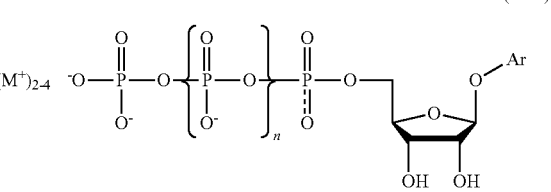

As indicated above, another aspect of the invention provides a compound of Formula IIA:

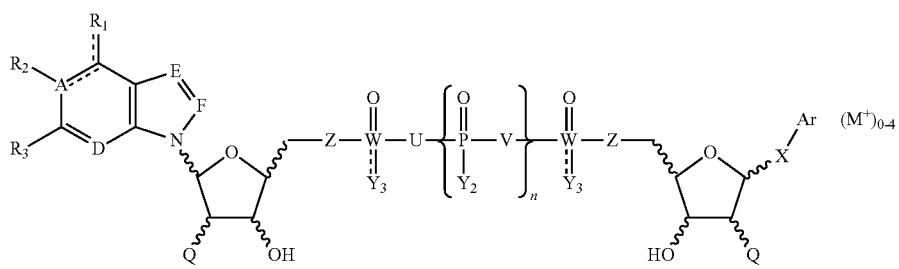

A specific value for n is O. Other specific values for n include 1 or 2.

A specific value for W is P or S, provided that when W is S, Y$_3$ is O;

A specific value for M is Na$^+$. Other specific values for M include K$^+$ and NH$_4^+$.

A specific group of compounds of formula IA are compounds of formula IA-1

A specific value for R$_1$ is H. Another specific value for R$_1$ is methyl. Another specific value for R$_1$ is ethyl. Another specific value for R$_1$ is NH. Another specific value for R$_1$ is N-methyl. Another specific value for R$_1$ is NH$_2$.

A specific value for R$_2$ is H. Another specific value for R$_2$ is methyl. Alternatively, R$_2$ may be absent.

A specific value for R$_3$ is H. Another specific value for R$_3$ is methyl. Another specific value for R$_3$ is ethyl.

Specific values for A, D, and E are N or CH. Further, a specific value for A, D, and E is N. A specific value for F is N.

A specific value for Ar is phenyl. Another specific value for Ar is pyridyl. Another specific value for Ar is

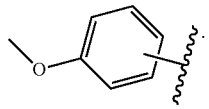

Another specific value for Ar is

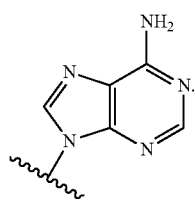 [SMILES: *n1cnc2c(N)ncnc21]

Another specific value for Ar is

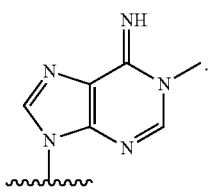 [SMILES: *n1cnc2c(=N)n(C)cnc21]

Another specific value for Ar is

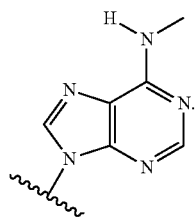 [SMILES: *n1cnc2c(NC)ncnc21]

Another specific value for Ar is

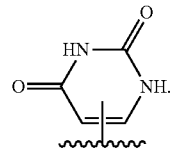

The Ar group can be optionally substituted with up to 3 groups, each independently selected from halo, hydroxy, alkyl, alkoxy, carboxy, cyano, nitro, sulfonamido, sulfonate, amino, imino, alkylamino and di-alkylamino; provided that when X is O, Ar is neither unsubstituted phenyl, anilino, nor 4-nitrophenyl.

A specific value for X is a bond. Another specific value for X is O. Other specific values for X include N, S, S(O), S(O$_2$), N(R'), —C(O)N(R')—, and —(CH$_2$)$_m$X$^1$—; wherein X$^1$ is O, S, S(O), S(O$_2$), or N(R'); R' is H, alkyl, or aralkyl; and m is 0, 1, 2, or 3.

A specific value for Q is H. Another specific value for Q is OH. Other specific values for Q include methoxy, ethoxy, fluoro, chloro, trifluoromethyl, NH$_2$, N(H)Me, N(H)Et, (Me)$_2$N, or (Et)$_2$N.

A specific value for U is O. Another specific value for U is NH. Another specific value for U is methyl amino diradical. Another specific value for U is ethyl amino diradical.

A specific value for V is O. Another specific value for V is NH. Another specific value for V is methyl amino diradical. Another specific value for V is ethyl amino diradical.

Specific values for Y$_2$ and Y$_3$ are O$^-$; and S$^-$. Other specific values for Y$_2$ and Y$_3$ include substituted or unsubstituted methoxy, ethoxy, trifluoromethoxy, phenoxy, benzyloxy, or cyclopropyl-, butyl-, pentyl- or hexyloxy, any of which may be optionally substituted.

A specific value for Z is O. Another specific value for Z is NH. Another specific value for Z is methylamino diradical.

A specific value for n is 0. Other specific values for n include 1 or 2.

A specific value for W is P or S, provided that when W is S, Y$_3$ is O;

A specific value for M is Na$^+$. Other specific values for M include K$^+$ and NH$_4^+$.

A specific group of compounds of formula IIA are compounds of formula IIA-1

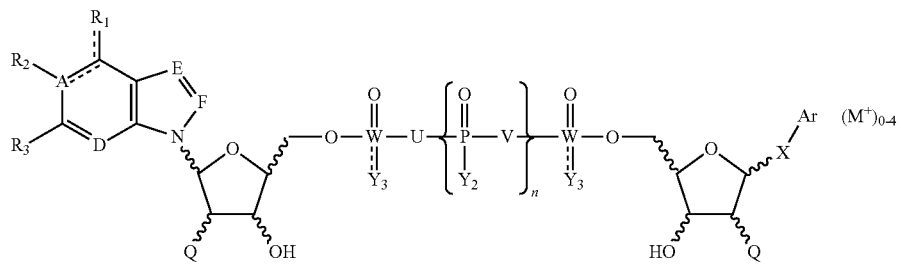

(IIA-1)

A specific group of compounds of formula IIA are compounds of formula IIA-2:
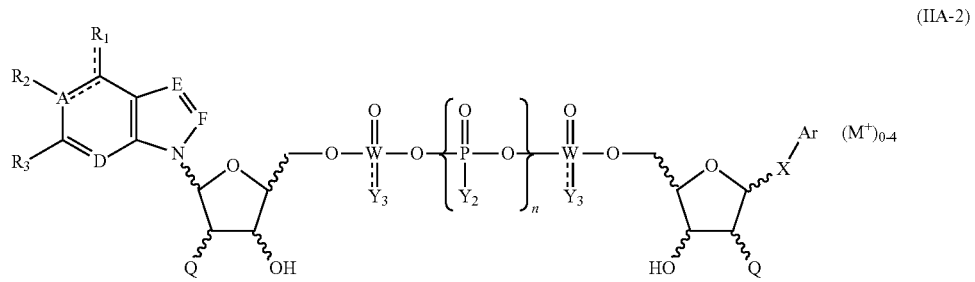
(IIA-2)
A specific group of compounds of formula IIA are compounds of formula IIA-3:
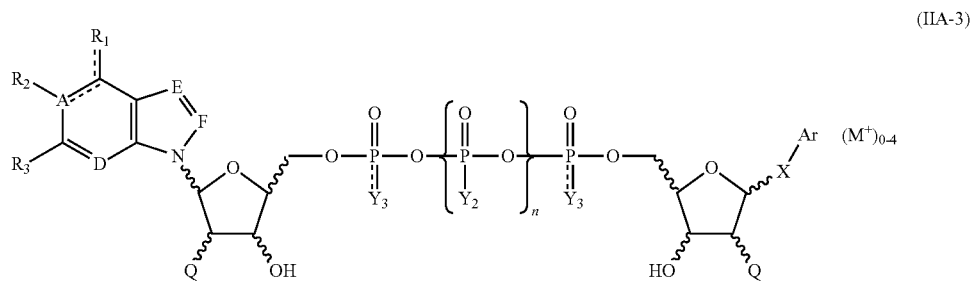
(IIA-3)
A specific group of compounds of formula IIA are compounds of formula IIA-4:
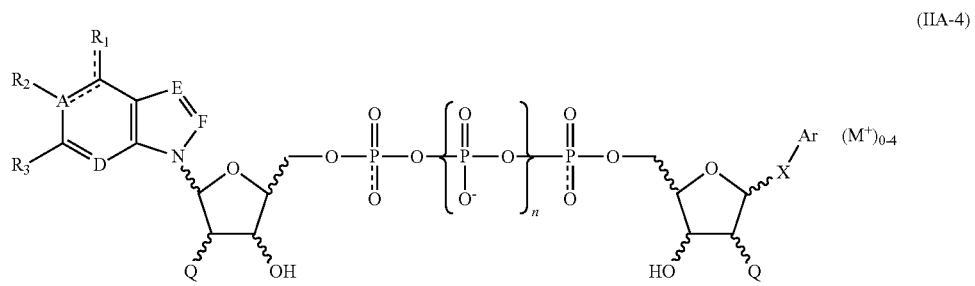
(IIA-4)
A specific group of compounds of formula IIA are compounds of formula IIA-5:
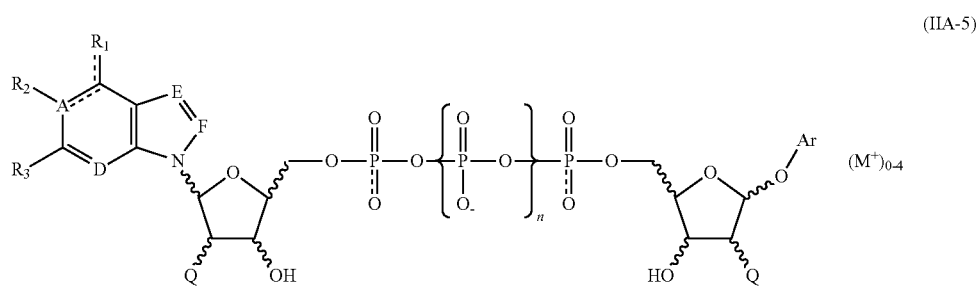
(IIA-5)

A specific group of compounds of formula IIA are compounds of formula IIA-5a:

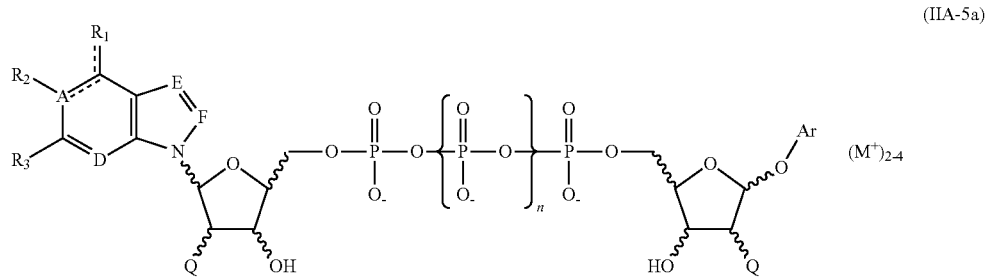

(IIA-5a)

A specific group of compounds of formula IIA are compounds of formula IIA-6:

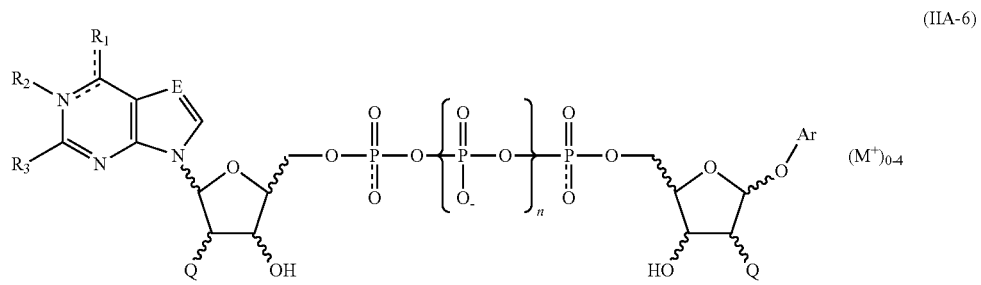

(IIA-6)

A specific group of compounds of formula IIA are compounds of formula IIA-7:

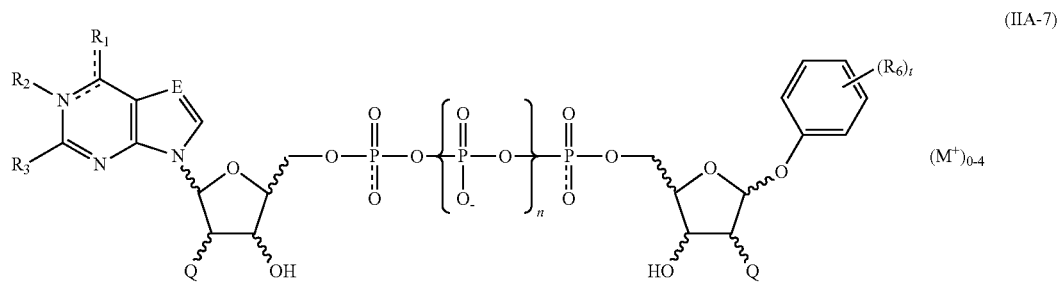

(IIA-7)

wherein $R_6$ represents independently for each occurrence halo, hydroxy, alkyl, alkoxy, carboxy, cyano, nitro, sulfonamido, sulfonate, amino, alkylamino, or di-alkylamino; and t is 1, 2, or 3.

A specific group of compounds of formula IIA are compounds of formula IIA-7a:

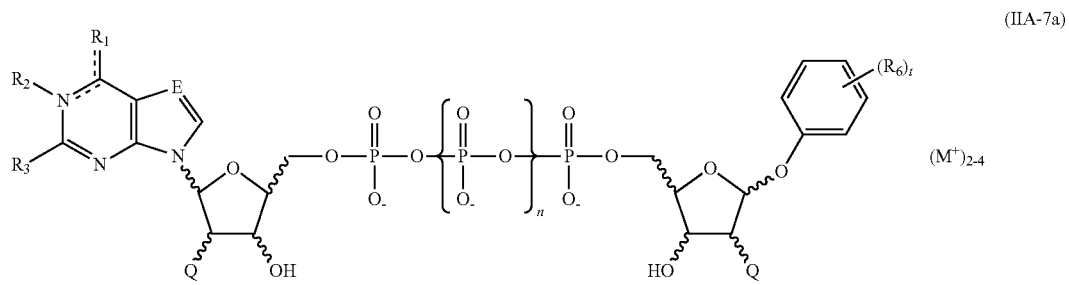

(IIA-7a)

wherein $R_6$ represents independently for each occurrence halo, hydroxy, alkyl, alkoxy, alkylamino, or di-alkylamino; and t is 1 or 2.

A specific group of compounds of formula IIA are compounds of formula IIA-8:

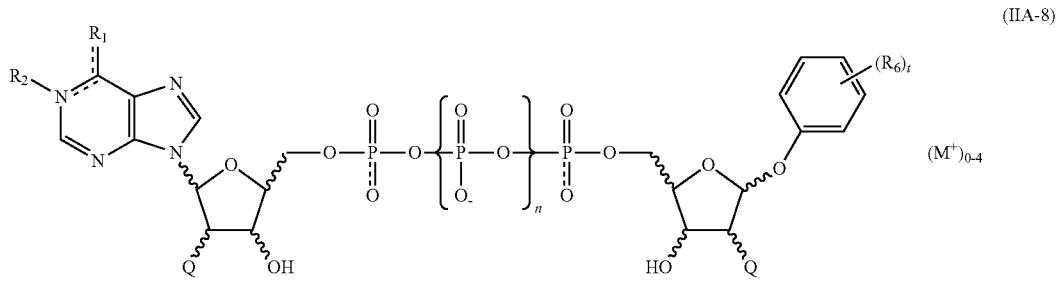

(IIA-8)

wherein:

$R_1$ is H, oxo, lower alkoxy, lower alkylamino, lower dialkylamino, imino, lower alkyl-substituted imino, lower thioalkyl, aryl, substituted or unsubstituted lower alkyl, or lower alkyl-substituted aryl;

$R_2$ is absent or is lower alkyl, lower alkoxy, lower alkyl-substituted aryl, aralkyl, or cycloalkyl;

$R_6$ represents independently for each occurrence halo, hydroxy, alkyl, alkoxy, carboxy, cyano, nitro, sulfonamido, sulfonate, amino, alkylamino, or di-alkylamino; and t is 1, 2, or 3.

A specific group of compounds of formula IIA are compounds of formula IIA-9:

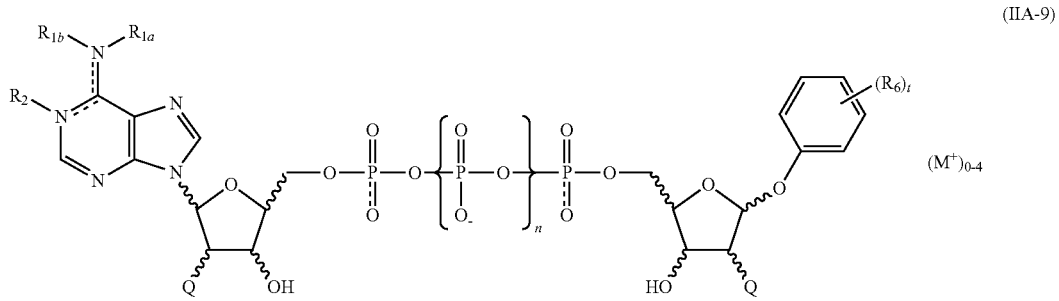

(IIA-9)

wherein:

$R_{1a}$ is absent or is H or alkyl;

$R_{1b}$ is H or alkyl;

$R_2$ is absent or is lower alkyl, lower alkoxy, lower alkyl-substituted aryl, aralkyl, or cycloalkyl;

$R_6$ represents independently for each occurrence halo, hydroxy, alkyl, alkoxy, carboxy, cyano, nitro, sulfonamido, sulfonate, amino, alkylamino, or di-alkylamino; and t is 1, 2, or 3.

A specific group of compounds of formula IIA are compounds of formula IIA-10:

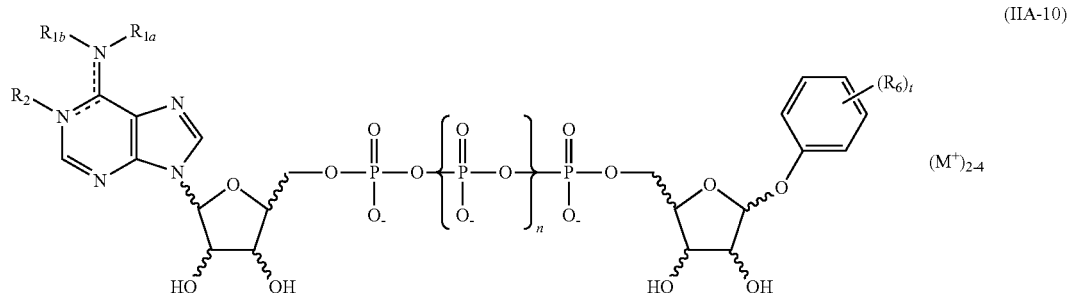

(IIA-10)

wherein:
R$_{1a}$ is absent or is H or C$_{1-5}$alkyl;
R$_{1b}$ is H or C$_{1-5}$alkyl;
R$_2$ is absent or C$_{1-5}$alkyl;
R$_6$ represents independently for each occurrence C$_{1-5}$alkyl or C$_{1-5}$alkoxy; and
t is 1 or 2.

As described above, another aspect of the invention provides a compound of Formula IIB:

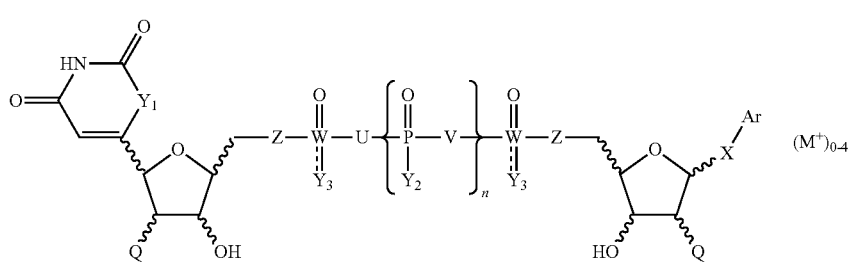

(IIB)

A specific value for Ar is phenyl. Another specific value for Ar is pyridyl. A specific value for Ar is phenyl. Another specific value for Ar is pyridyl. Another specific value for Ar is

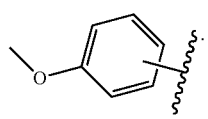

Another specific value for Ar is

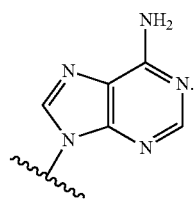 [SMILES: *n1cnc2c(N)ncnc21]

Another specific value for Ar is

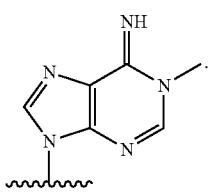 [SMILES: *n1cnc2c(=N)n(C)cnc21]

Another specific value for Ar is

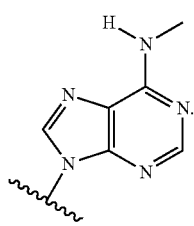

Another specific value for Ar is

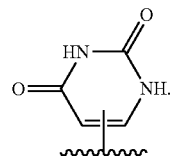

The Ar group can be optionally substituted with up to 3 groups, each independently selected from halo, hydroxy, alkyl, alkoxy, carboxy, cyano, nitro, sulfonamido, sulfonate, amino, imino, alkylamino and di-alkylamino; provided that when X is O, Ar is neither unsubstituted phenyl, anilino, nor 4-nitrophenyl.

A specific value for X is a bond. Another specific value for X is O. Other specific values for X include N, S, S(O), S(O$_2$), N(R'), —C(O)N(R')—, and —(CH$_2$)$_m$X$^1$—; wherein X$^1$ is O, S, S(O), S(O$_2$), or N(R'); R' is H, alkyl, or aralkyl; and m is 0, 1, 2, or 3.

A specific value for Q is H. Another specific value for Q is OH. Other specific values for Q include methoxy, ethoxy, fluoro, chloro, trifluoromethyl, NH$_2$, N(H)Me, N(H)Et, (Me)$_2$N, or (Et)$_2$N.

A specific value for U is O. Another specific value for U is NH. Another specific value for U is methyl amino diradical. Another specific value for U is ethyl amino diradical.

A specific value for V is O. Another specific value for V is NH. Another specific value for V is methyl amino diradical. Another specific value for V is ethyl amino.

Specific values for Y$_2$ and Y$_3$ are O$^-$ and S$^-$. Other specific values for Y$_2$ and Y$_3$ include substituted or unsubstituted methoxy, ethoxy, trifluoromethoxy, phenoxy, benzyloxy, or cyclopropyl-, butyl-, pentyl- or hexyloxy, any of which may be optionally substituted.

A specific value for Y$_1$ is NH. A specific value for Y$_1$ is CH$_2$.

A specific value for Z is O. Another specific value for Z is NH. Another specific value for Z is methylamino diradical.

A specific value for n is 0. Other specific values for n include 1 or 2.

A specific value for W is P or S, provided that when W is S, Y$_3$ is O;

A specific value for M is Na$^+$. Other specific values for M include K$^+$ and NH$_4^+$.

A specific group of compounds of formula IIB are compounds for formula IIB-1.

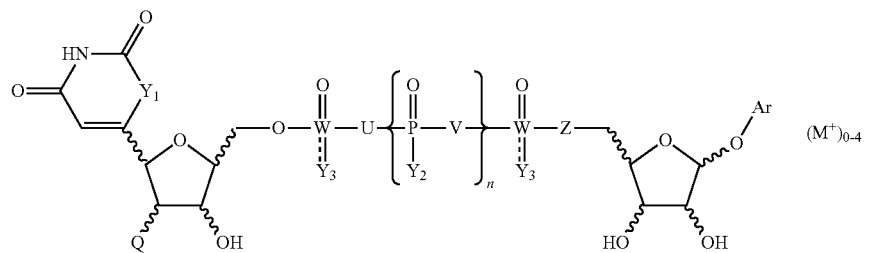
(IIB-1)
Another specific group of compounds of formula IIB are compounds for formula IIB-2.
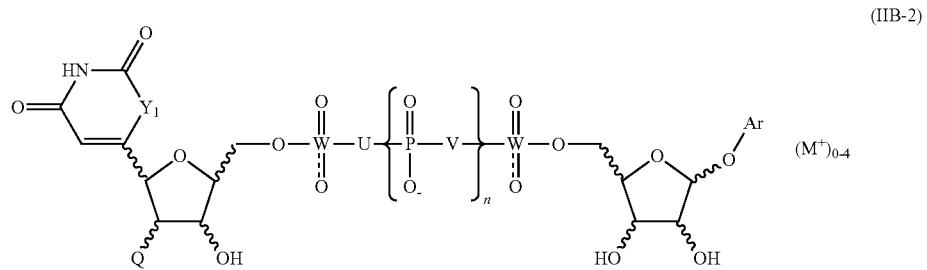
(IIB-2)
Another specific group of compounds of formula IIB are compounds for formula IIB-3.
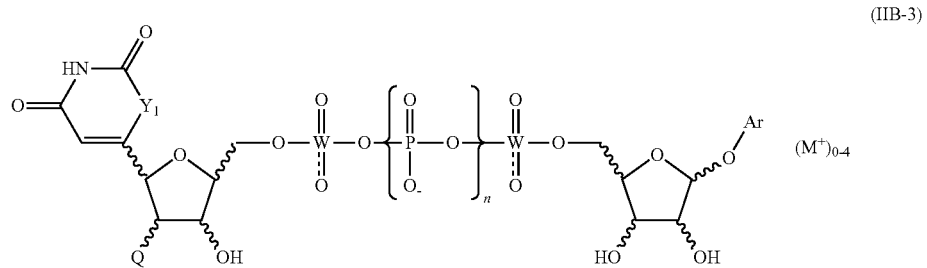
(IIB-3)
Another specific group of compounds of formula IIB are compounds for formula IIB-4.
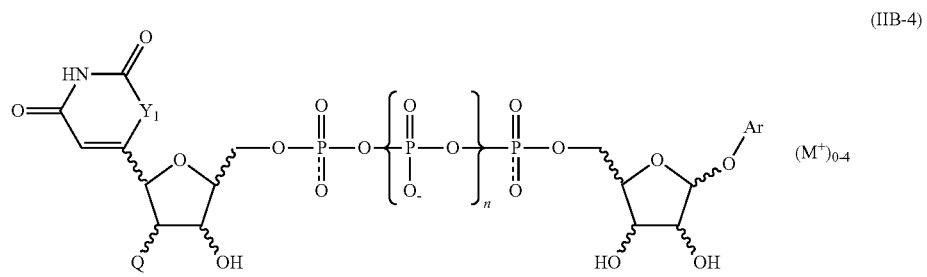
(IIB-4)

As described above, another aspect of the invention provides a compound of Formula IIIA.

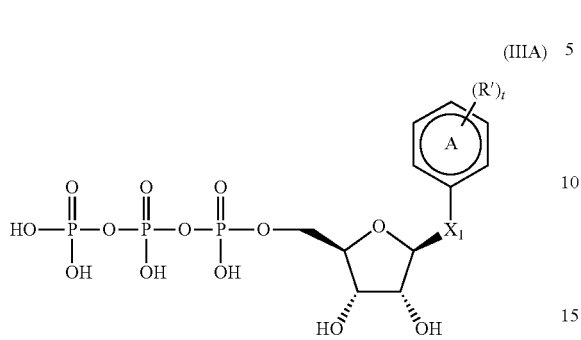
(IIIA)

A specific value for

is phenyl. Another specific value for

is pyridyl;

A specific value for $X_1$ is a bond. Another specific value for $X_1$ is O. Other specific values for $X_1$ include NH, N(alkyl), —N(alkyl)-C(O)—, —C(O)N(alkyl)-, —N(alkyl)-CH$_2$—, —CH$_2$—N(alkyl)-, —CH$_2$N(alkyl)-C(O)—, or —C(O)N(alkyl)-CH$_2$—.

A specific value for R' is fluoro. Another specific value for R' is methoxy. Another specific value for R' is nitro. A specific value for t is 1 or 2.

As described above, another aspect of the invention provides a compound of formula IV:

Another specific value for Ar is

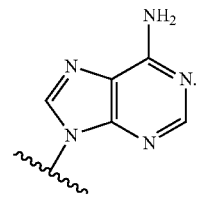 [SMILES: *n1cnc2c(N)ncnc21]

Another specific value for Ar is

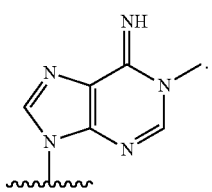 [SMILES: *n1cnc2c(=N)n(C)cnc21]

Another specific value for Ar is

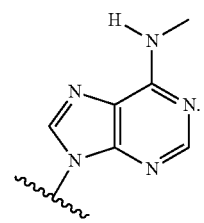 [SMILES: *n1cnc2c(NC)ncnc21]

Another specific value for Ar is

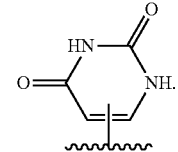

The Ar group can be optionally substituted with up to 3 groups, each independently selected from halo, hydroxy,

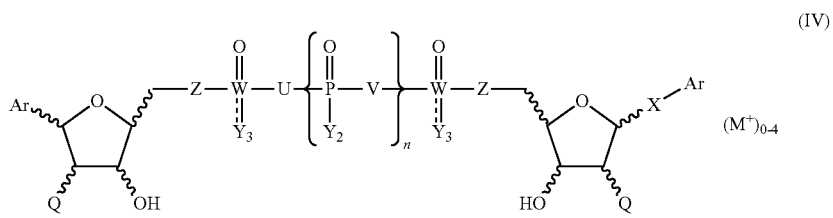
(IV)

A specific value for Ar is phenyl. Another specific value for Ar is pyridyl. Another specific value for Ar is

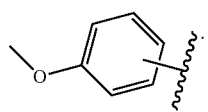

alkyl, alkoxy, carboxy, cyano, nitro, sulfonamido, sulfonate, amino, imino, alkylamino and di-alkylamino; provided that when X is O, Ar is neither unsubstituted phenyl, anilino, nor 4-nitrophenyl.

A specific value for X is a bond. Another specific value for X is O. Other specific values for X include N, S, S(O), S(O$_2$), N(R'), —C(O)N(R')—, or —(CH$_2$)$_m$X$^1$—; wherein X$^1$ is O, S, S(O), S(O$_2$), or N(R'); R' is H, alkyl, or aralkyl; and m is 0, 1, 2, or 3.

A specific value for Q is H. Another specific value for Q is OH. Other specific values for Q include methoxy, ethoxy, fluoro, chloro, trifluoromethyl, $NH_2$, N(H)Me, N(H)Et, $(Me)_2N$, or $(Et)_2N$.

A specific value for U is O. Another specific value for U is NH. Another specific value for U is methyl amino diradical. Another specific value for U is ethyl amino diradical.

A specific value for V is O. Another specific value for V is NH. Another specific value for V is methyl amino diradical. Another specific value for V is ethyl amino diradical.

Specific values for $Y_2$ and $Y_3$ are $O^-$ and $S^-$. Other specific values for $Y_2$ and $Y_3$ include substituted or unsubstituted methoxy, ethoxy, trifluoromethoxy, phenoxy, benzyloxy, or cyclopropyl-, butyl-, pentyl- or hexyloxy, any of which may be optionally substituted.

A specific value for Z is O. Another specific value for Z is NH. Another specific value for Z is methylamino diradical.

A specific value for n is 0. Other specific values for n include 1 or 2.

A specific value for W is P or S, provided that when W is S, $Y_3$ is O.

A specific value for M is $Na^+$. Other specific values for M include $K^+$ and $NH_4^+$.

A specific group of compounds of formula IV are compounds of formula IV-1

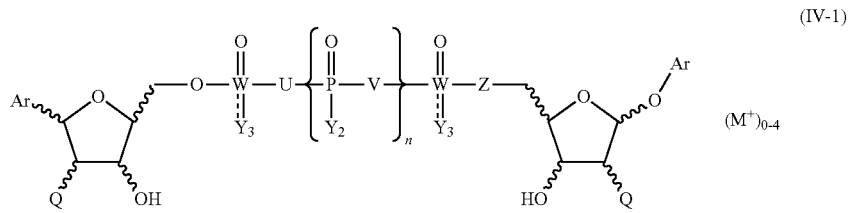

(IV-1)

Another specific group of compounds of formula IV are compounds of formula IV-2.

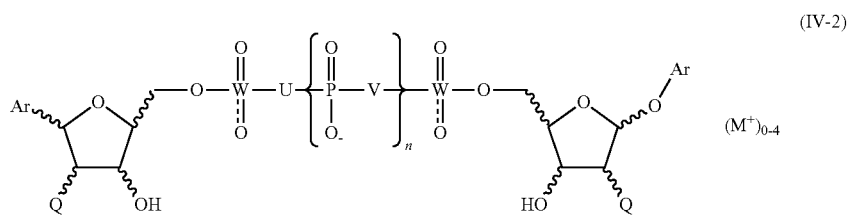

(IV-2)

Another specific group of compounds of formula IV are compounds of formula IV-3.

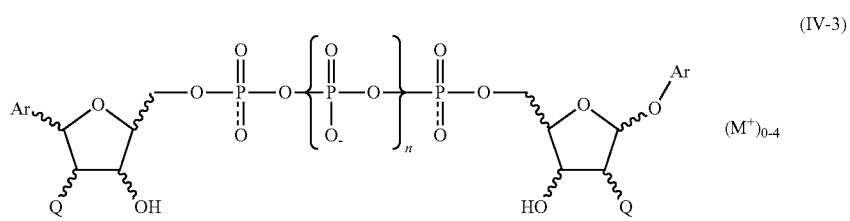

(IV-3)

Another specific group of compounds of formula IV are compounds of formula IV-4.

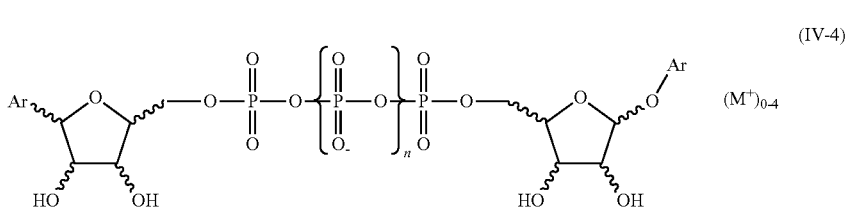

(IV-4)

The invention provides compounds that are selective agonists of the $P2Y_2$ purinergic receptor. These compounds are therefore contemplated to be useful in treating chronic obstructive pulmonary diseases such as chronic bronchitis, PCD, and cystic fibrosis; they are also contemplated to be useful in the treatment of immobilized patients at risk for developing pneumonia. Furthermore, because of their general ability to clear retained mucus secretions and stimulate ciliary beat frequency, the compounds described herein are contemplated to be useful in the treatment of sinusitis and otitis media. The compounds described herein are also contemplated to be useful for facilitating expectorating sputum specimens for diagnostic purposes in patients at risk for lung cancer, pneumonia, and other infectious diseases. The compounds described herein may also be used in treating asthma, and may enhance the performance of athletes by increasing the clearance of mucous secretions from the lungs; and may be used for wound healing.

Mucins are high molecular weight glycoproteins secreted or expressed by goblet and nongoblet epithelial cells of mucosal tissues. Mucins can form mucus, a highly hydrated gel. It is contemplated that the compounds described herein can modulate mucin or mucus production. Influences on mucus secretion include, e.g., the quantity and type of mucin (e.g., sulfomucin and/or sialomucin), viscosity changes, hydrogen ion retardation, hydrophobicity, phospholipid content changes, glycosylation and sulfation, macromolecular assembly, surface tension, adhesivity, transport properties, elastic modulus, tensile properties, rigidity factors, recoil factors, spinnbarkeit, sperm penetration qualities, consistency, cellularity, ferning, and the like. The mucosal surface can be a lung surface, a sinus, a nasal passage, an ear canal, an eye, a throat, or a reproductive canal (e.g., a female reproductive canal).

The invention provides compounds that are selective $P2Y_2$ agonists, and thus, these compounds are contemplated to be useful in treating mammals suffering from chronic obstructive pulmonary diseases such as chronic bronchitis, acute bronchitis, acute exacerbations of chronic bronchitis, PCD, cystic fibrosis, as well as preventing pneumonia due to immobility. Where cilia are impaired or absent, compounds described herein may enhance cough clearance. Because of their ability to clear retained mucus secretions and stimulate ciliary beat frequency, the compounds described herein are contemplated to be useful in treating acute and chronic sinusitis and otitis media. By enhancing secretion clearance, the compounds are useful as protection before or after exposure to inhaled biological warfare agents. They can also be used to enhance lung imaging by clearing secretions from the lungs prior to obtaining the image.

Compounds and methods described herein can change the constitutive and stimulated secretions of the local reproductive system, including those of the vagina, cervix, uterus, fallopian tube, Bartholin or vestibular glands and urethral secretions. Thus, methods and compositions described herein are contemplated to influence the function of the mucus genes found in the reproductive system, including, but not limited to genes that control mucus production in the cervix, uterus, and Bartholin's glands and other parts of the reproductive system with mucus secreting cells. The squamous epithelium of the lower genital tract and epithelial cells of the cervix can be treated by the methods described herein. Included are methods to influence or change the secretary effects of the mucus genes, mucus secreting cells and cells that influence the properties of secretory and cell surface mucins of all the above mentioned glands of the reproductive system.

In one embodiment, the method increases secretion of mucus in vaginal or cervical epithelial cells. In another embodiment, the method involves activating $P2Y_2$ or $P2Y_1$ receptors in vaginal or cervical cells. Such methods can prevent or treat vaginal dryness in a mammal, or maintain or enhance the normal protective function of vaginal mucus in a mammal.

The invention also provides pharmaceutical compositions comprising adenosine analog compounds, and the use of these compounds and compositions in the prevention or treatment of diseases in which P2Y receptors are involved.

The invention further provides compositions comprising an adenosine analog compound described herein and a pharmaceutically acceptable carrier.

The invention further provides methods of modulating P2Y activity comprising contacting a P2Y receptor with a compound described herein.

The invention further provides methods of treating a disease associated with expression or activity of a P2Y receptor in a patient comprising administering to the patient a therapeutically effective amount of a compound described herein.

The invention further provides a method of treating constipation comprising administering to a subject in need thereof a therapeutically effective amount of a compound described herein. Constipation is generally regarded as a condition in which the feces persists for a long time in the bowel and compels the patient to experience difficulty in discharging it from the bowel. The constipation is often induced by the fact that the series of defecating mechanisms are impeded by various causes. In certain instances, constipation is complicated by such symptoms as abdominalgia, abdominal distention, lumbago, headache, and anorexia. In certain embodiments, the constipation is associated with irritable bowel syndrome. In certain embodiments, the constipation is chronic constipation. A variety of conditions and medications can be associated with chronic constipation, for example, primary or idiopathic constipation can be broadly divided into slow-transit constipation (i.e., colonic inertia) and dyssynergic defecation (i.e., anismus, outlet obstruction, pelvic floor dysfunction, pelvic floor dyssynergia, defecatory dysfunction). Physiologic abnormalities in patients with slow-transit constipation can include abnormal postprandial colonic motor function, autonomic dysfunction, and reduced numbers of colonic enterochromaffin cells and interstitial cells of Cajal. Dyssynergic defecation can occur as a consequence of the inability to coordinate actions of the abdominal musculature, anorectum, and pelvic floor musculature. An example is puborectalis dyssynergia, wherein the puborectalis sling fails to relax or paradoxically contracts with straining. This prevents straightening of the anorectal angle, which should precede the notinal passage of stool. Structural abnormalities, such as a large rectocele, rectal intussusception, and obstructing sigmoidocele, can also contribute to constipation. Chronic constipation can also be a result of medications, endocrine disorders, and neurological disorders. For example, medications such as opiates, psychotropics, anticonvulsants, anticholinergics, dopaminergics, calcium channel blockers, bile acid binders, nonsterodial anti-inflammatory drugs, and supplements, i.e., calcium and iron, can initiate the onset of chronic constipation. Endocrine disorders such as diabetes mellitus, hypothyroidism, hyperparathyroidism, and pheochromocytoma similarly provoke the onset of chronic constipation. Moreover, chronic constipation can occur with both systemic (e.g., diabetic neuropathy, Parkinson's disease and Shy-Drager syndrome) and traumatic (e.g., spinal chord lesions) neurological disorder. Accordingly, methods of treating the above conditions or chronic constipation, functional constipation, chronic functional constipation, or IBS-C, by administering a therapeutically effective amount of a compound described herein are contemplated.

The invention further provides a compound described herein for use in therapy.

The invention further provides use of a compound described herein for the manufacture of a medicament for treating a disease associated with expression or activity of a P2Y receptor.

The capacity of the compounds of the invention to have agonostic activity on P2Y function can be determined using a suitable screen (e.g., high throughput assay). For example, an agent can be tested in an in vitro assay such as intracellular calcium mobilization, IP1 accumulation, mucin secretion, ciliary beat frequency and short current circuit assays. The potency of compounds can also be assessed by ex vivo assays such as short circuit current, chloride secretion and fluid secretion assays where epithelial preparations are used. For antagonistic activity identical in vitro assays can be used.

The compounds of formula I described herein, and compositions thereof are useful in the modulation of P2Y receptor activity, particularly $P2Y_2$. Accordingly, the compounds described herein are contemplated to increase at least one function or characteristic of a mammalian P2Y receptor, for example, a human $P2Y_2$ receptor. The ability of a compound to increase such a function can be demonstrated, e.g., in a binding assay (e.g., ligand binding or promoter binding), and/or cellular response function (e.g., mucus secretion or ciliary beat frequency).

"Prodrug" includes compounds that are transformed in vivo to yield a compound of the above formulae or a pharmaceutically acceptable salt, hydrate or solvate of the compound. The transformation may occur by various mechanisms, such as through hydrolysis in blood. For example, if a compound of the above formulae or a pharmaceutically acceptable salt, hydrate or solvate of the compound contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound described herein contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy) ethyl, 1-methyl-1-(($C_1-C_6$)alkanoyloxy)ethyl $(C_1-C_6)$ alkoxycarbonyloxymethyl, N—$(C_1-C_6)$alkoxycarbonylaminomethyl, succinoyl, $(C_1-C_6)$alkanoyl, α-amino$(C_1-C_4)$ alkanoyl, arylacyl and α-aminoacyl, or α-aminoacyl-α-aminoacyl, where each α-aminoacyl group is independently selected from the naturally occurring L-amino acids, P(O) $(OH)_2$, —P(O)(O$(C_1-C_6)$alkyl$)_2$ or glycosyl (the radical resulting from the removal of a hydroxyl group of the hemiacetal form of a carbohydrate).

If a compound described herein incorporates an amine functional group, a prodrug can be formed by the replacement of a hydrogen atom in the amine group with a group such as R-carbonyl, RO-carbonyl, or NRR'-carbonyl where R and R' are each independently $(C_1-C_{10})$alkyl, $(C_3-C_7)$cycloalkyl, or benzyl, or R-carbonyl is a natural α-aminoacyl or natural α-aminoacyl-natural α-aminoacyl, or C(OH)C(O)OY$^1$ wherein Y$^1$ is H, $(C_1-C_6)$alkyl or benzyl, —C(OY$^2$)Y$^3$ wherein Y$^2$ is $(C_1-C_4)$alkyl and Y$^3$ is $(C_1-C_6)$alkyl, carboxy $(C_1-C_6)$alkyl, amino$(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino, morpholino, piperidin-1-yl or pyrrolidin-1-yl.

The compounds of the above formulae may contain asymmetric or chiral centers, and, therefore, exist in different stereoisomeric forms. It is intended that all stereoisomeric forms of the compounds of the above formulae as well as mixtures thereof, including racemic mixtures, form part of the invention. In addition, the invention embraces all geometric and positional isomers. For example, if a compound of the above formulae incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column.

The compounds of the above formulae may exist in unsolvated as well as solvated forms with pharmaceutically acceptable solvents such as water, ethanol, and the like, and it is intended that the invention embrace both solvated and unsolvated forms.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled compounds of the above formulae (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the above formulae can generally be prepared by following procedures analogous to those disclosed in the Schemes and/or in the Examples hereinbelow, by substituting an isotopically labeled reagent for a non-isotopically labeled reagent.

"Individual", "patient," or "subject" are used interchangeably and include to any animal, including mammals, preferably mice, rats, other rodents, rabbits, dogs, cats, swine, cattle, sheep, horses, or primates, and most preferably humans. The compounds described herein can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods described herein is desirably a mammal in whom modulation of P2Y receptor activity is desired. "Modulation" includes antagonism (e.g., inhibition), agonism, partial antagonism and/or partial agonism.

Treatment of, or treating, a mammal includes modulation of mucus levels to enhance or diminish mucus production in the mammal. In some embodiments, such treatment involves alleviating or diminishing the symptoms of cystic fibrosis, pneumonia, vaginal dryness, or chronic obstructive pulmonary diseases such as chronic bronchitis or Primary Ciliary Dyskinesia in a mammal. The treatment, therefore, can include alleviation or diminishment of more than one problem associated with mucus secretion in a mammal.

The term "therapeutically effective amount" means the amount of the subject compound that will elicit the biological or medical response of a tissue, system, animal or human that is being sought by the researcher, veterinarian, medical doctor or other clinician. The compounds described herein can be administered in therapeutically effective amounts to treat a disease. Alternatively, a therapeutically effective amount of a compound is the quantity required to achieve a desired therapeutic and/or prophylactic effect.

Suitable pharmaceutical agents that may be used in combination with the compounds described herein include agents that alleviate the disease symptoms or have curative effects by a mechanism other than ones mediated through P2Y receptors.

"Combination therapy" (or "co-therapy") includes the administration of a P2Y modulator described herein and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" embraces administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds described herein and the other pharmacologically active agent may be administered to a patient simultaneously, sequentially or in combination. It will be appreciated that when using a combination, the adenosine analog compound described herein and the other pharmacologically active agent may be in the same pharmaceutically acceptable carrier and therefore administered simultaneously. They may be in separate pharmaceutical carriers such as conventional oral dosage forms which are taken simultaneously. The term "combination" includes the case where the compounds are provided in separate dosage forms and are administered sequentially.

The compounds described herein may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

The compounds described herein can be administered to a patient at dosage levels in the range of from about 0.01 to about 100 mg per day. As used herein, the term "unit dose" or "unit dosage" refers to physically discrete units that contain a predetermined quantity of a compound described herein calculated to produce a desired therapeutic effect. The dosage to be administered may vary depending upon the physical characteristics of the patient, the severity of the patient's symptoms, and the means used to administer the drug. The specific dose for a given patient is usually set by the judgment of the attending physician. It is also noted that the compounds of the invention can be used in sustained release, controlled release, and delayed release formulations, which forms are also well known to one of ordinary skill in the art.

Daily doses of the compositions described herein can vary as well. Such daily doses can range, for example, from about 0.001 mg/day to about 50 mg/day, from about 0.01 mg/day to about 25 mg/day, from about 0.1 mg/day to about 12 mg/day, from about 0.1 mg/day to about 8 mg/day, from about 0.1 mg/day to about 4 mg/day, and from about 0.1 mg/day to about 2 mg/day of at least one peptide or compound described herein.

For treatment of respiratory disorders, concentration levels from about $10^{-7}$ M to about $10^{-1}$ M, preferably $10^{-5}$ to $10^{-3}$ M, or doses of about 1-400 mg, may be used. For ophthalmic and sinus uses, 0.1 to 10.0% concentrations may be used. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound, the age, body weight, general health, sex, diet, time of administration, route of administration, and rate of absorption, distribution, metabolism and excretion, drugs used in combination, and the type and severity of the particular disease undergoing therapy.

For intravaginal administration, the therapeutic agents may be formulated as is known in the art for direct application to the vaginal area. Forms chiefly conditioned for vaginal application take the form, for example, of milks, gels, dispersions, microemulsions, lotions thickened to a greater or lesser extent, impregnated pads, ointments, aerosol formulations (e.g., sprays or foams), creams, pastes, jellies, sprays, and aerosols. Alternatively, the composition can be formulated to be part of an adhesive polymer, such as polyacrylate or acrylate/vinyl acetate copolymer.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the active compound, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The pharmaceutical compositions of this invention may be used in the form of a pharmaceutical preparation, for example, in solid, semisolid or liquid form, which contains one or more of the compounds described herein, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound described herein may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The preparation of an aqueous composition that contains a composition described herein or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

It is contemplated that a compound described herein may be in the form of a pharmaceutically acceptable salt. Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, α-keto glutaric, α-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives of the compounds of the invention such as the compounds quaternized by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide, e.g., chloride, bromide or iodide. Yet other examples of pharmaceutically acceptable salts also include internal salts such as N-oxides. The invention encompass pharmaceutically acceptable salts of the compounds described herein, such as, but not limited to, an alkali metal salt such as sodium or potassium; an alkaline earth metal salt such as magnesium or calcium; manganese; or an ammonium or tetraalkyl ammonium salt, i.e., $NX_4^+$ (wherein X is $C_{1-4}$ alkyl). Pharmaceutically acceptable salts have the desired biological activity of the parent compound. In a preferred instance, the pharmaceutically acceptable salt does not have substantial undesired toxicological effects. Salts of the present invention encompass mono-, di-, tri- and tetra-cations which may contain a single cation or mixed cations.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including creams.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermoclysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 75% of the weight of the unit, or preferably between about 25%-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Advantageously, the invention also provides kits for use by a consumer. Such kits include a suitable dosage form such as those described above and instructions describing the method of using such dosage form. The instructions would direct the consumer or medical personnel to administer the dosage form according to administration modes known to those skilled in the art. Such kits could advantageously be packaged and sold in single or multiple kit units.

Since the invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: an adenosine analog compound described herein and a second pharmaceutical agent as described above. The kit comprises a container (e.g., a divided bottle or a divided foil packet). Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Methods for preparing the compounds described herein are illustrated in the following synthetic schemes. The following schemes are given for the purpose of illustrating the invention, but not for limiting the scope or spirit of the invention. In reference to compound ArXH, numerous ArXH compounds are amenable to the present invention and can be obtained from commercial sources or prepared based on literature procedures. It is contemplated that X can be a heteroatom, such as oxygen or nitrogen.

Scheme 1

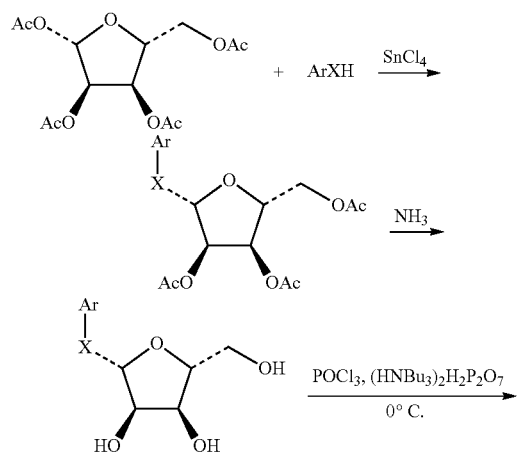

-continued

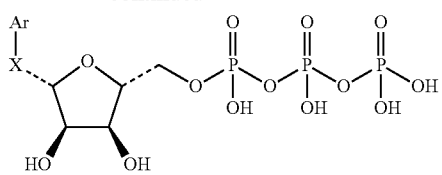

Scheme 2

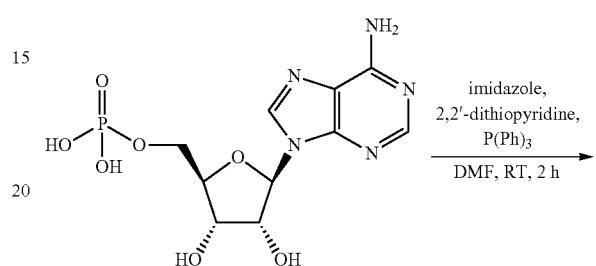

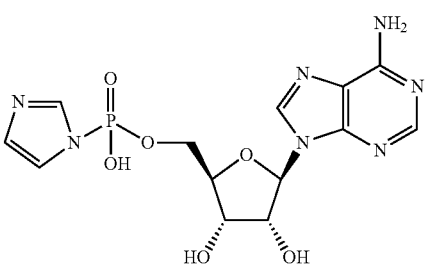

Scheme 3

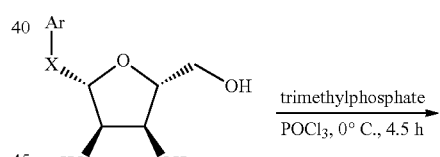

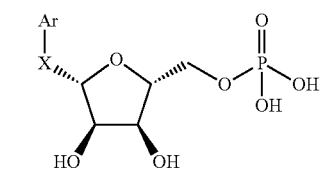

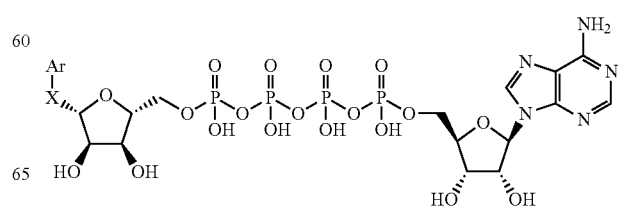

Scheme 4

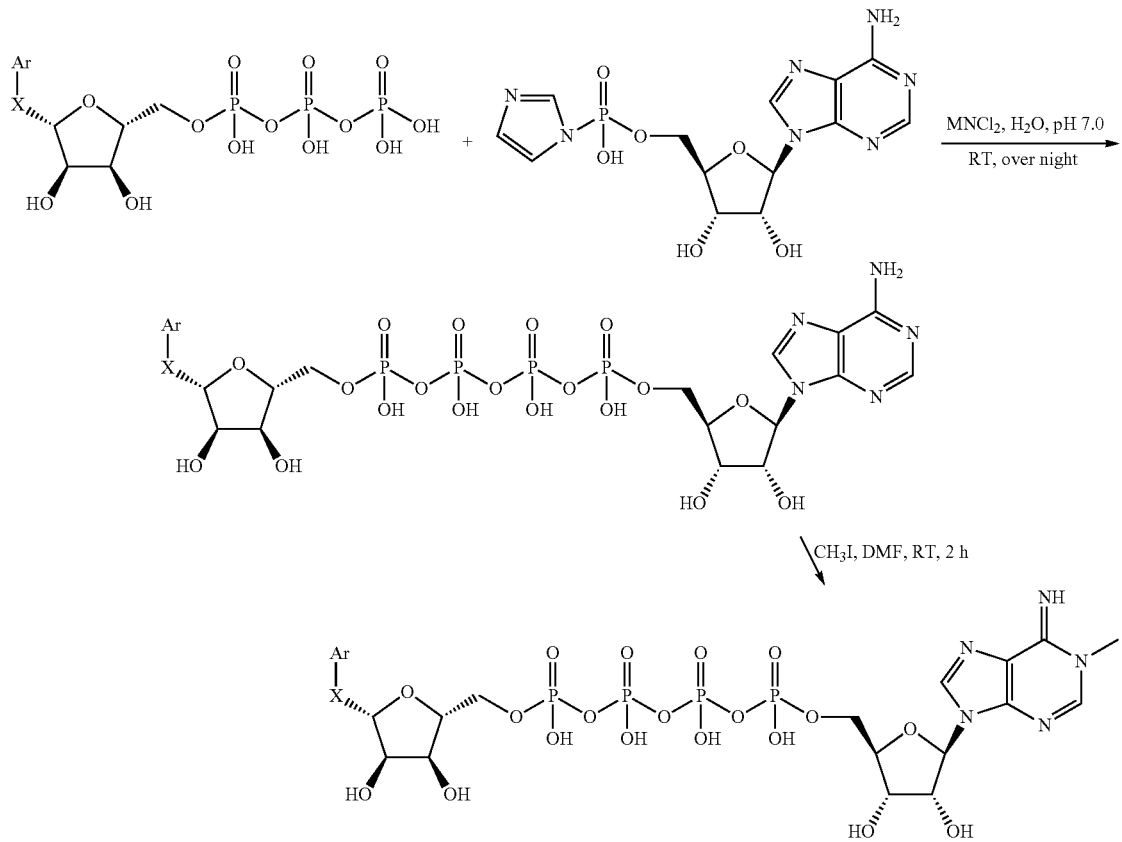

EXAMPLES

The invention now being generally described, will be more readily understood by reference to the following examples, which are included merely for purposes of illustration of certain aspects and embodiments of the present invention, and are not intended to limit the invention.

Chemicals and General Methods:

All chemicals were purchased from Sigma-Aldrich unless stated otherwise.

Ion Exchange Chromatography:

The crude product was dissolved in 500 mL water. The pH of the solution was adjusted to 7.5, and was applied to a Q Sepharose Fast flow column (500×25, bed volume 240 mL) and eluted using a gradient from 50 mM triethylammonium bicarbonate (TEAB) pH 8.0 to 2 M TEAB pH 8.0 (94 fractions, 20 mL each). Fractions containing the product were pooled and evaporated to dryness. Excess of buffer was removed by evaporation with 50 mL methanol (4 times). The residue was purified by preparative HPLC chromatography.

Preparative Reverse Phase (RP) HPLC Chromatography:

The ion exchange-purified product was dissolved in 2 mL water, applied to a PRONTOSIL column (120-5-C18-AQ, 5 μm, 250×20) and eluted by a gradient from 100% 0.1 M triethylammonium acetate pH 7.0 to 30% 0.1 M triethylammonium acetate pH 7.0/70% acetonitrile within 60 minutes, flow rate 15 mL/min. Fractions containing the product were pooled and evaporated to dryness. Excess of buffer was removed by evaporation with 5 mL water (4 times).

Preparation of the Sodium Salts:

After preparative HPLC, triethylammonium salts of the nucleotides were dissolved in 1 to 3 mL methanol. The solution was treated with 1 mL 1 M NaClO$_4$ in acetone. Acetone (20 mL) was added and the resulting solid was filtered and dried in vacuo.

Example 1

Preparation of the Tri-(n-butyl)-ammonium Pyrophosphate

Tetrasodium diphosphate decahydrate (2.23 g, 5 mmol) was dissolved in water (50 mL), the solution was applied to a column of Dowex 50WX8 (100 mL) in the pyridinium form, and the column was washed with 300 mL water-methanol (1:1). The eluate was directly dropped into a cooled (ice water) and stirred solution of tri-n-butylamine (2.38 mL, 10 mmol) in methanol. The solution was evaporated to dryness and re-evaporated twice with methanol and finally with anhydrous DMF (30 mL) on an oil pump.

Example 2

Preparation of 4-Methoxyphenyl(tri-o-acetyl-α,β-D-ribofuranoside)

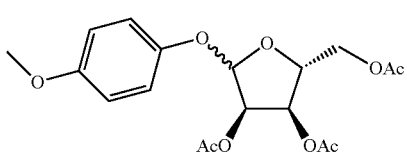 [SMILES: COc1ccc(OC2O[C@H](COC(C)=O)[C@@H](OC(C)=O)[C@H]2OC(C)=O)cc1]

A solution of 1,2,3,5-tetra-O-acetyl-β-D-ribofuranose (2.2 g, 7 mmol) in CH$_2$Cl$_2$ (30 mL) at 0° C. was treated with SnCl$_4$ (850 μl, 7 mmol) in 3 mL CH$_2$Cl$_2$. After 15 minutes, dried 4-methoxyphenol (1 g, 8 mmol) was added and the suspension was treated for approximately 1 minute in an ultrasonic bath until the mixture became homogenous. The mixture was then stirred at 0° C. for 10 minutes. The cooling bath was removed and the solution was allowed to reach room temperature over 40 minutes. Stirring was continued for an additional 1 hour. The reaction mixture was poured into a saturated solution of NaHCO$_3$ (40 ml, 0° C.) and extracted with CHCl$_3$ (2×50 mL). The combined organic extracts (white emulsion) were co-evaporated with ethanol (3×100 mL) to dryness. The yellow residue was suspended in CHCl$_3$ and applied to a column of silica gel. Elution with CHCl$_3$-EtOH, gradient (98:2 to 90:10) and evaporation of the appropriate fractions gave an anomeric mixture of the title compound as yellow oil (1.1 g, 2.9 mmol, 41%).

Example 3

Preparation of 4-Methoxyphenyl-β-D-ribofuranoside

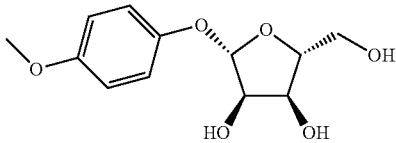 [SMILES: COc1ccc(O[C@@H]2O[C@H](CO)[C@@H](O)[C@H]2O)cc1]

4-Methoxyphenyl(tri-O-acetyl-α,β-D-ribofuranoside) (1 g, 2.65 mmol) was dissolved in 20 mL of methanol and treated with a solution of NH$_3$ (25%, 5 mL) in water. After 24 hours at room temperature, the solution was co-evaporated with water (2×50 mL) and ethanol (2×50 mL). The resulting yellow oil was dissolved in 20 mL toluene-methanol (4:1) and applied to a column of silica gel and the product was eluted with toluene-methanol (4:1). Evaporation of the product fractions gave the 4-methoxyphenyl-α,β-D-ribofuranoside as a white solid (510 mg). This material appears as a single spot on TLC analysis. The α and β anomers were separated by preparative RP-HPLC and yielded 380 mg (1.48 mmol, 56%) of the 4-methoxyphenyl-β-D-ribofuranoside and 95 mg (0.37 mmol) of the 4-methoxyphenyl-α-D-ribofuranoside. MS (ESI): m/z 279.2 (M+23)$^+$.

Example 4

Preparation of 4-Methoxyphenyl-β-D-ribofuranoside-5'-monophosphate

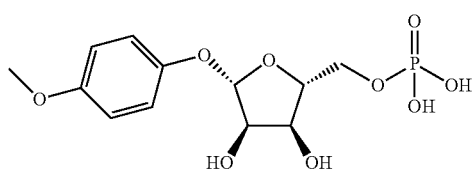 [SMILES: COc1ccc(O[C@@H]2O[C@H](COP(=O)(O)O)[C@@H](O)[C@H]2O)cc1]

4-Methoxyphenyl-β-D-ribofuranoside (890 mg, 3.47 mmol) was dissolved in 18 mL of trimethylphosphate under argon atmosphere. The solution was cooled to 0° C. and after 10 minutes, 412 μL (4.52 mmol) phosphorous oxychloride was added carefully. After 4.5 hours, excess POCl$_3$ was removed in vacuo over 10 minutes. The remaining solution of the initially formed dichlorophosphate intermediate was quenched by adding 30 mL of 1M triethylammonium bicarbonate buffer (pH 7.5) at 0° C. Purification by ion exchange chromatography gave the title product (0.8 mmol, 24%) as triethylammonium salt, which was subsequently used in the next step without further purification. MS (ES) m/z 335 [M−H]$^-$.

Example 5

Preparation of 4-Methoxyphenyl-β-D-ribofuranosidyl-5'-triphosphate (Compound A)

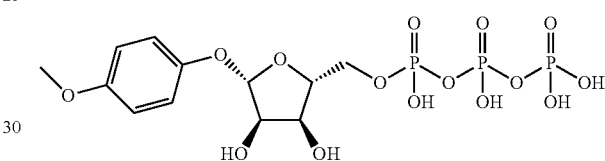

Method A:

4-Methoxyphenyl-β-D-ribofuranosidyl-5'-monophosphate triethylammonium salt (0.8 mmol) was dissolved in methanol (20 mL) and treated with tri-n-butylamine (850 μL, 2.4 mmol). The solution was evaporated to dryness. The residue was dissolved in methanol and re-evaporated twice. Subsequently, this procedure was repeated three times with anhydrous DMF (15 mL) using an oil pump. The residue was dissolved in 12 mL anhydrous DMF and then N,N'-carbonyldiimidazole (CDI) (1.3 g, 8 mmol) was added and the mixture was stirred for 1.5 hours at room temperature. After the excess CDI was degraded by addition of dry methanol (526 μL, 13 mmol), pyrophosphoric acid tri-n-butylammonium salt (5.5 mmol) in dry DMF (10 mL) was added. The resulting suspension was stirred at room temperature and the progress of the reaction was monitored by HPLC. After 4 days, the reaction mixture was diluted to 2000 mL, and pH was adjusted to 7.5. Purification by ion exchange chromatography yielded the title product as triethylammonium salt, which was subsequently precipitated as its sodium salt (180 mg, 0.32 mmol, 40%). MS (ES): m/z 495 [M−H]$^-$, 598 [M+C$_6$H$_{15}$N]$^+$.

Method B:

4-Methoxyphenyl β-D-ribofuranoside (0.258 g, 1.0 mmol) was dissolved in 5 mL of trimethylphosphate under an argon atmosphere. The solution was cooled to 0° C. and 0.4 Ml of 2,6-lutidine was added. After 10 minutes, 0.2 mL (2.2 mmol) of phosphorous oxychloride was added carefully. After 1 hour, excess POCl$_3$ was removed in vacuo over 10 minutes.

The remaining solution, dichlorophosphate intermediate was then treated with a freshly prepared 1 M solution of tri-(n-butyl)-ammonium pyrophosphate (5 mL, 5 mmol) in DMF. After 2 minutes, the reaction was quenched by adding 50 mL of 0.25 M triethylammonium bicarbonate buffer (pH 7.5). Purification by ion exchange chromatography gave a crude product (134 mg) as triethylammonium salt, which was subsequently purified by RP HPLC and precipitated as its sodium salt (55 mg, 0.09 mmol, 9.8%). $^1$H NMR (D$_2$O): δ 7.10 (d, 2H), 6.95 (d, 2H), 5.55 (s, 1H), 4.50 (m, 1H), 4.35 (m, 1H), 4.25 (m, 1H), 4.05-4.20 (m, 2H), 3.80 (s, 3H); MS (ESI): m/z 495.4 (M$^+$, negative mode).

Example 6

Preparation of Adenosine-5'-phosphoroimidazolate

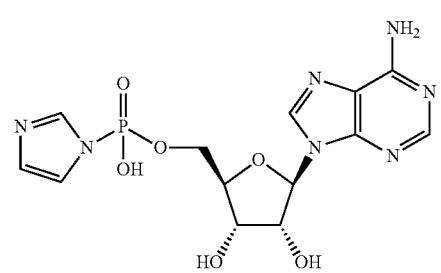 [SMILES: Nc1ncnc2c1ncn2[C@@H]1O[C@H](COP(=O)(O)n2ccnc2)[C@@H](O)[C@H]1O]

Adenosine-5'-monophosphate (6 mmol) was dissolved in 1:1 mixture of methanol and water (100 mL) and the resulting solution was treated with tri-n-butylamine (7.2 mL, 30 mmol). The solution was evaporated to dryness. The residue was dissolved in methanol and re-evaporated twice. Subsequently, this procedure was repeated twice with anhydrous DMF (50 mL) using an oil pump. The residue was dissolved in 30 mL of anhydrous DMF and then imidazole (4.1 g, 60 mmol), 2,2'-dipyridyldisulfide (10.6 g, 48 mmol) and triphenylphosphine (12.6 g, 48 mmol) were added. The solution was stirred for 2 hours at room temperature. It was then treated with 10 mL of 1 M sodium perchlorate solution in acetone (30 mL). The sodium salt of adenosine-5'-phosphoroimidazolate was obtained as a white precipitate, which was collected by centrifugation, washed with acetone (5×30 mL), and then dried in a desiccator. The product (2.25 g, 5.3 mmol, 88%) was used in the next step without further purification.

Example 7

Preparation of Adenosine-5'-triphosphoroimidazolate

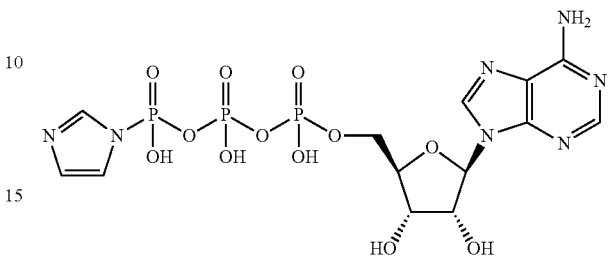

Adenosine-5'-triphosphate sodium salt (18.1 mmol) was dissolved in water (40 mL). The resulting solution was applied to a column of Dowex 50WX8 (200 mL) in its pyridinium form, and eluted with a water-methanol mixture (1:1, 500 mL). The eluate was directly added dropwise to a cooled (ice water) and stirred solution of tri-n-butylamine (37.7 mL, 158.4 mmol) in 100 mL methanol. The solution was evaporated to dryness and re-evaporated twice with methanol and finally with anhydrous DMF (200 mL) using an oil pump. The residue was dissolved in 200 mL of anhydrous DMF and then imidazole (12.2 g, 180 mmol), 2,2'-dithiopyridine (31.6 g, 144 mmol) and triphenylphosphine (37.7 g, 144 mmol) were added. The solution was stirred at room temperature for 4 hours and then it was treated with 100 mL of a 1 M sodium perchlorate solution in acetone (30 mL). The sodium salt of adenosine-5'-triphosphoroimidazolate was obtained as a white precipitate, which was collected by centrifugation, washed with acetone (5×200 mL), and then dried in a desiccator. The title product (10.5 g, 17.4 mmol, 96%) was used in the next step without further purification.

Example 8

Preparation of Compound B

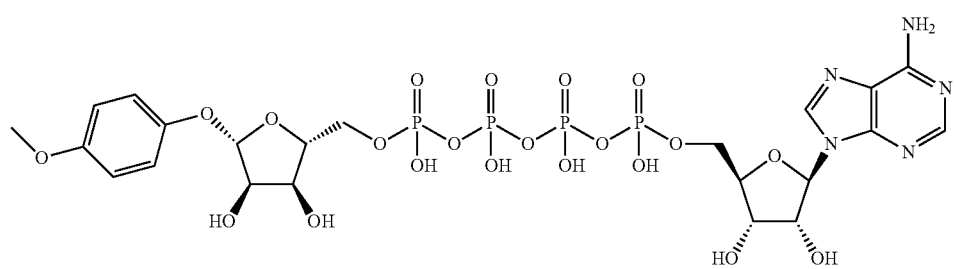 [SMILES: COc1ccc(O[C@@H]2O[C@H](COP(=O)(O)OP(=O)(O)OP(=O)(O)OP(=O)(O)OC[C@H]3O[C@@H](n4cnc5c(N)ncnc54)[C@H](O)[C@@H]3O)[C@@H](O)[C@H]2O)cc1]

Method A:

To a solution of methoxyphenyl-β-D-ribonucleosidyl-5'-triphosphate sodium salt (478 mg, 0.85 mmol) in water (3 mL), $MnCl_2 \times 2H_2O$ (688 mg, 4.25 mmol) was added. The resulting solution was slowly added to a solution of adenosine-5'-phosphorimidazolate (1.8 g, 4.25 mmol) in 0.2 M N-ethylmorpholine-HCl buffer pH 7.0 (7 ml). The suspension (pH 4.5) was treated carefully with a 2 M HCl solution until the precipitate completely dissolved (pH 2.8). The reaction mixture was stirred over night at room temperature and the mixture was then treated with a 1 M versenol solution until the suspension became clear. Subsequently, it was diluted to 2000 mL with water, pH was adjusted to 7.5 and the solution applied to an ion exchange chromatography column. The fractions containing the product were combined and the title product was isolated as triethylammonium salt (335 mg, 0.28 mmol, 33%), which was used in the next step without further purification. MS (ES) m/z 824 $[M-H]^-$.

Method B:

4-Methoxyphenyl-β-D-ribofuranosidyl-5'-monophosphate sodium salt (2.61 mmol) was dissolved in water (3 mL) and then $MnCl_2 \times 2H_2O$ (1.26 g, 7.83 mmol) was added. The resulting solution was slowly added to a solution of adenosine-5'-triphosphorimidazolate (4.8 g, 7.8 mmol) in 0.2 M N-ethylmorpholine-HCl buffer pH 7.0 (7 ml). The suspension (pH 4.5) was treated carefully with 2 M HCl solution until the precipitate dissolved almost completely (pH 2.0). The reaction mixture was stirred over night at room temperature. Then it was treated with 1 M versenol solution until the suspension became clear. Subsequently, it was diluted to 2000 mL with water and pH was adjusted to 7.5. The resulting solution was applied to ion exchange chromatography column. The fractions containing the product were pooled and the product was isolated as a triethylammonium salt (136 mg, 0.11 mmol, 4%), which was used in the next step without further purification. MS (ES) m/z 824 $[M-H]^-$.

Example 9

Preparation of Compound C

Compound B as its triethylammonium salt (335 mg, 0.28 mmol) was dissolved in methanol (5 mL) and treated with tri-n-butylamine (2 mL, 8.4 mmol). The solution was evaporated to dryness. The residue was dissolved in methanol and re-evaporated twice. This procedure was repeated three more times with anhydrous DMF (20 mL) using an oil pump. The residue was then dissolved in 12 mL of anhydrous DMF and iodomethane (50 mL, 803 mmol) was added. The reaction mixture was stirred at room temperature for 2 hours. The solvent was evaporated to dryness. The residue was dissolved in water (250 mL), and the pH of the solution was adjusted (from 1.2) to 7.5 with 1M triethylammonium bicarbonate (pH 11.0). Purification by ion exchange chromatography yielded the product (105 mg, 12.6%) and the starting non-methylated compound (240 mg) as triethylammonium salts. The product was subsequently purified by RP HPLC and precipitated as its sodium salt (32 mg, 0.035 mmol, 12.6%). MS (ES): m/z 838 $[M-H]^-$, 941 $[M+C_6H_{15}N]^+$, 1042 $[M+2 \times C_6H_{15}N]^+$.

Example 10

Preparation of
1-Methyl-Adenosine-5'-monophosphate

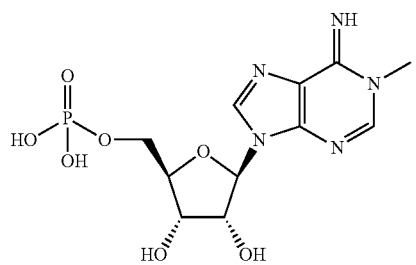

Adenosine-5'-monophosphate sodium salt (10 g, 24.7 mmol) was dissolved in water (50 mL). The resulting solution was applied to a Dowex 50WX8 column (200 mL) in the pyridinium form. Subsequently the column was washed with 600 mL water-methanol (1:1). The eluate was directly collected into a cold, stirred solution of tri-n-butylamine (17.6 mL, 74.1 mmol) in methanol. The solvent was evaporated to dryness, dissolved again in methanol and re-evaporated twice. This procedure was repeated twice more with anhydrous DMF (700 mL) using an oil pump. The residue was dissolved in 700 mL anhydrous DMF. Iodomethane (50 mL, 803 mmol) was then added and the reaction mixture was

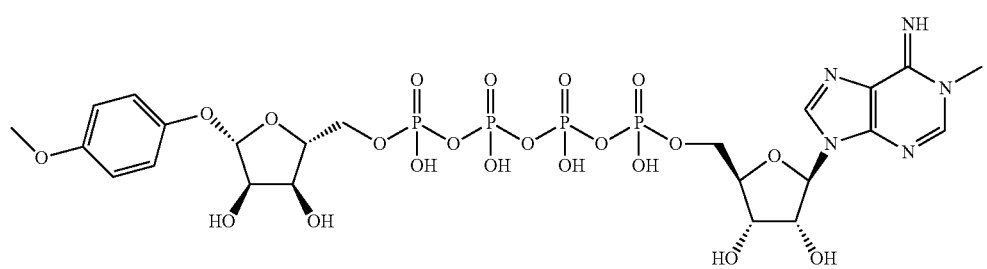

stirred at room temperature for 20 hours. The solution was evaporated to dryness. The residue was dissolved in water (1000 mL) and the pH of the solution was adjusted from 1.2 to 7.5 with 1M triethylammonium bicarbonate (pH 11.0). Purification by ion exchange chromatography yielded the product (2.1 g, 23%) as a sodium salt, and was used in the next steps without further purification: MS (ES) m/z 362 [M+H]+, 360 [M+Na]+.

Example 11

Preparation of 1-Methyladenosine-5'-phosphoroimidazolate

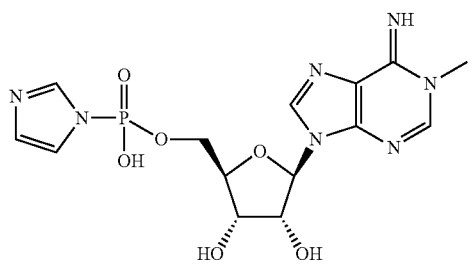 [SMILES: Cn1cnc2c(ncn2[C@@H]2O[C@H](COP(=O)(O)n3ccnc3)[C@@H](O)[C@H]2O)c1=N]

1-Methyl-adenosine-5'-monophosphate sodium salt (4 mmol) was dissolved in water (5 mL), the solution was applied to a column of Dowex 50WX8 (75 ml) in its pyridinium form, and eluted with a water-methanol mixture (1:1, 150 mL). The elutate was directly added in a dropwise manner to an ice-cooled, stirred solution of tri-n-butylamine (2.38 mL, 10 mmol) in methanol. The solution was evaporated to dryness, re-evaporated twice with methanol, and finally with anhydrous DMF (30 mL) using an oil pump. The residue was dissolved in 25 mL anhydrous DMF and then imidazole (2.45 g, 36 mmol) 2,2'-dithiopyridine (7.9 g, 36 mmol) and triphenylphosphine (9.4 g, 36 mmol) were added. The solution was stirred overnight at room temperature and then it was concentrated to 10 mL. To the concentrated solution, acetone (50 ml) and 1 M sodium perchlorate solution in acetone (16 mL) were added. The sodium salt of 1-methyladenosine-5'-phosphoroimidazolate was obtained (1.9 g, 80%) as white precipitate, which was collected by centrifugation. It was washed with acetone (3×50 mL), dried in a desiccator, and used in the next step without further purification.

Example 12

Preparation of Compounds C, D, and E

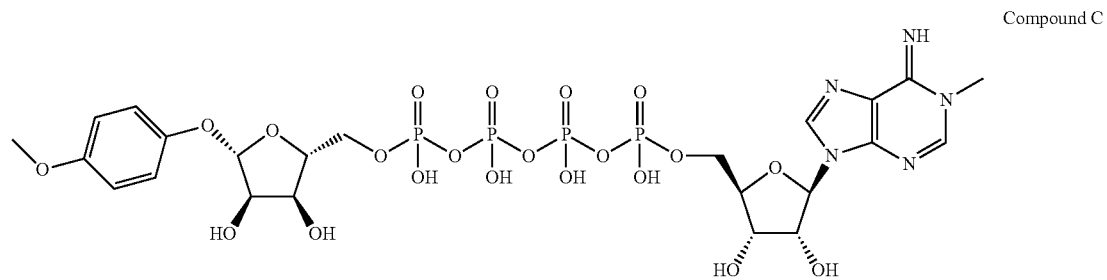

Compound C

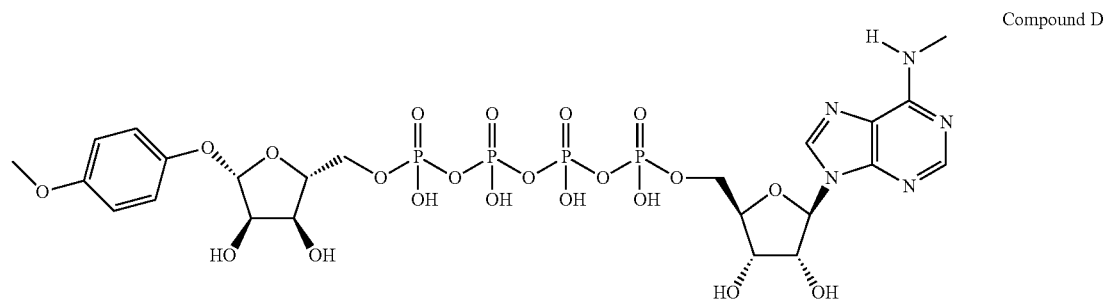

Compound D

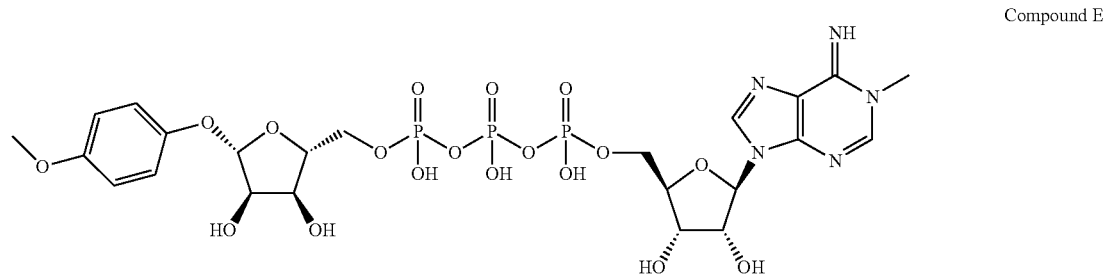

Compound E

To a solution of 4-methoxyphenyl-β-D-ribofuranosidyl-5'-triphosphate sodium salt (100 mg, 0.178 mmol) in water (4 mL), MnCl₂×2H₂O (143 mg, 0.89 mmol) and 0.2 M N-ethylmorpholine-HCl buffer pH 7.0 (2 mL) were added. The pH of the reaction mixture was carefully adjusted from 2.0 to 7.0 with a 2 M NaOH solution. The resulting suspension was added to 1-methyladenosine-5'-phosphoroimidazolate sodium salt (1.2 g, 2.7 mmol) and stirred at room temperature for 6 days. The reaction mixture was then treated with 1 M versenol solution until the suspension became clear. Subsequently, it was diluted to 2000 mL with water, the pH was adjusted to 7.5 and the solution applied to an ion exchange chromatography column. The resulting crude products were then purified by RP HPLC and the fractions containing the products were applied to an ion exchange chromatography column with triethylammonium bicarbonate buffer in order to remove the triethylammonium acetate buffer salts from the RP HPLC run. The products were precipitated as sodium salts.

Compound C: (19 mg, 0.022 mmol, 12%): ¹H-NMR (D₂O): δ 3.59 (s, 3H, O—CH₃), 3.65 (s, 3H, N1-CH₃), 3.95-5.80 (m, 10H, ribose), 5.23 (s, 1H, H-1"), 5.95 (d, 1H, H-1'), 6.65 (d, 2H, aromatic), 6.75 (d, 2H, aromatic), 8.25 (s, 1H, heterocyclic), 8.45 (s, 1H, heterocyclic); MS (ES): m/z 838 [M–H]⁻, 941 [M+C₆H₁₅N]⁺.

Compound D: (6.3 mg, 0.0069 mmol, 3.8%): ¹H-NMR (D₂O): δ 3.59 (s, 3H, O—CH₃), 3.65 (s, 3H, N1-CH₃), 3.95-5.80 (m, 10H, ribose), 5.23 (s, 1H, H-1"), 5.95 (d, 1H, H-1'), 6.65 (d, 2H, aromatic), 6.75 (d, 2H, aromatic), 8.25 (s, 1H, heterocyclic), 8.45 (s, 1H, heterocyclic); MS (ES): m/z 838 [M–H]⁻, 941 [M+C₆H₁₅N]⁺.

Compound E: (3.7 mg, 0.0046 mmol, 2.5%): ¹H-NMR (D₂O): δ 2.90 (s, 3H, N6-CH₃), 3.59 (s, 3H, O—CH₃), 3.95-5.80 (m, 10H, ribose), 5.20 (s, 1H, H-1"), 5.95 (d, 1H, H-1'), 6.65 (dd, 4H, aromatic), 8.20 (s, 1H, heterocyclic), 8.45 (s, 1H, heterocyclic); MS (ES): m/z 758 [M–H]⁻, 861 [M+C₆H₁₅N]⁺.

Example 13

Preparation of 2-Nitroacetophenone hydrazone

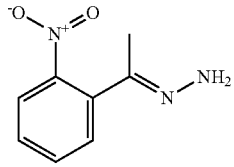

A solution of 2-nitroacetophenone (12.28 g, 0.074 mol) in ethanol (100 mL) was treated with hydrazine hydrate (10.24 g, 0.163 mol) and glacial acetic acid (4.2 mL, 0.074 mol) and the mixture was heated at reflux for 3 hours. The solvent was then evaporated in vacuo. The residue was dissolved in trichloromethane and extracted three times with water to remove the excess of hydrazine hydrate. Evaporation of the organic layer yielded the product (11 g, 0.06 mol, 81%), which was used in the next step without further purification.

Example 14

Preparation of Compound F

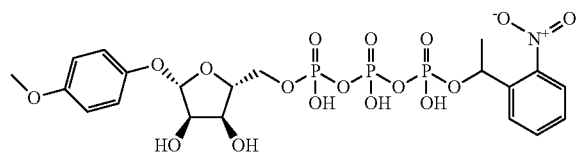

2-Nitroacetophenone hydrazone (62.7 mg, 0.35 mmol) in 15 mL diethyl ether was stirred with activated MnO₂ (250 mg, 2.88 mmol) for 5 minutes in the dark at room temperature. (All manipulations from this point on were carried out in the dark). MnO₂ was removed by filtration and the filtrate was added to a stirred solution of 4-methoxyphenyl-β-D-ribofuranosidyl-5'-triphosphate triethylammonium salt (25 mg, 0.035 mmol) in 15 mL water at pH 4.0. The mixture was stirred vigorously at room temperature and the progress of the reaction was monitored by analytical HPLC. After 19 hours, the aqueous phase was separated, washed twice with diethyl ether (50 mL), and diluted to 250 mL with water. The pH was then adjusted to 7.5 with 1 M NaOH and the solution was applied to an ion exchange chromatography column. The fractions containing the product were subsequently purified by RP HPLC chromatography. The product was precipitated as its sodium salt (7 mg, 0.01 mmol, 29%): ¹H-NMR (D₂O): δ 1.35 (d, 3H) 3.55 (s, 3H, —OCH₃), 3.80-3.95 (m, 2H), 4.00 (m, 1H), 4.10 (d, 1H), 4.25 (m, 1H), 5.35 (s, 1H), 5.75 (m, 1H), 6.70 (d, 2H), 6.85 (d, 2H), 7.25 (t, 1H), 7.55 (t, 1H), 7.65 (m, 1H), 7.80 (d, 1H); MS (ES): m/z 644 [M–H]⁻, 747 [M+C₆H₁₅N]⁺.

Example 15

Preparation of (3R,4S,5R)—N-(3-fluorophenyl)-3,4-dihydroxy-5-(hydroxymethyl)-N-methyltetrahydrofuran-2-carboxamide

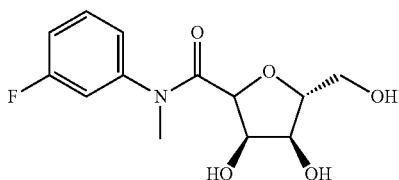 [SMILES: CN(C(=O)C1O[C@H](CO)[C@@H](O)[C@H]1O)c1cccc(F)c1]

(3R,4R,5R)-3,4-Bis(benzoyloxy)-5-(benzoyloxymethyl)tetrahydrofuran-2-carboxylic acid (3,4,6-tri-O-benzoyl-2,5-anhydro-D-allonic acid, 2 g, 4 mmol) was dissolved in anhydrous THF (40 mL) under argon atmosphere. To this, triphenylphosphine (2.1 g, 8 mmol) was added and the mixture was stirred until it was dissolved completely. To this clear solution, 2,2'-dipyridyldisulfide (1.8 g, 8 mmol) was added and the mixture was stirred at room temperature for 2 hours, after which, 3-fluoro-N-methylaniline (0.7 g, 5.6 mmol) was added and stirring was continued at room temperature for 16 hours. The solvent was evaporated to dryness, the residue was dissolved in chloroform (150 ml), the solution washed twice with 0.1M NaOH solution (100 mL), twice with 0.2 M HCl solution (100 mL), once with saturated NaHCO₃ solution (100 mL), and then dried over $Na_2SO_4$. The solution was evaporated to dryness and the residue was re-dissolved in methanolic ammonia (7M solution, 250 mL). The solution was stirred for 16 hours at room temperature and evaporated to dryness. The crude product was purified by silica gel chromatography using a mixture of chloroform-methanol (3:1) and evaporation of the appropriate fractions yielded the title compound as a colorless oil (0.5 g, 1.7 mmol, 42%): MS (ES) m/z 308 [M+Na]$^+$, 284 [M−H]$^−$.

Example 16

Preparation of ((2R,3S,4R)-5-((3-fluorophenyl)(methyl)carbamoyl)-3,4-dihydroxytetrahydrofuran-2-yl)methyltriphosphoric acid (Compound G)

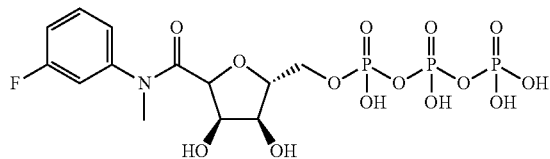 [SMILES: CN(C(=O)C1O[C@H](COP(=O)(O)OP(=O)(O)OP(=O)(O)O)[C@@H](O)[C@H]1O)c1cccc(F)c1]

(3R,4S,5R)—N-(3-Fluorophenyl)-3,4-dihydroxy-5-(hydroxymethyl)-N-methyltetrahydrofuran-2-carboxamide(N-(2,5-anhydro-D-allonoyl)-3-fluoro-N-methylaniline, 0.27 g, 0.9 mmol) was dissolved in 5 mL of trimethylphosphate under argon atmosphere. The solution was cooled to 0° C. and 0.4 mL of 2,6-lutidine was added. After 10 minutes, 0.15 mL (1.7 mmol) of phosphorous oxychloride was carefully added. After 1 hour, excess $POCl_3$ was removed in vacuo over 10 minutes. The remaining solution of the initially formed dichlorophosphate intermediate was then treated with a freshly prepared 1 M solution of tri-(n-butyl)-ammonium pyrophosphate (4.5 mL, 4.5 mmol) in DMF. After 2 minutes, the reaction was quenched by adding 50 mL of 0.25 M triethylammonium bicarbonate buffer (pH 7.5). Purification by ion exchange chromatography gave a crude product (134 mg) as a triethylammonium salt, which was subsequently purified by RP HPLC and precipitated as its sodium salt (120 mg, 0.2 mmol, 22%): $^1$H-NMR ($D_2O$): δ 3.27 (s, 3H, N—$CH_3$), 3.93-4.25 (br, m, 4H, H-3', H-4', H-5', H-5"), 4.31 (t, 1H, H-2'), 4.37 (d, 1H, H-1'), 7.20 (br, m, 3H, aromatic), 7.50 (m, 1H, aromatic); MS (ES) m/z 524 [M−H]$^−$.

Example 17

Preparation of (3R,4S,5R)-3,4-dihydroxy-5-(hydroxymethyl)-N-(3-methoxyphenyl)-N-methyltetrahydrofuran-2-carboxamide

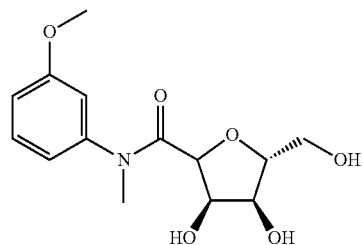 [SMILES: COc1cccc(N(C)C(=O)C2O[C@H](CO)[C@@H](O)[C@H]2O)c1]

(3R,4R,5R)-3,4-Bis(benzoyloxy)-5-(benzoyloxymethyl)tetrahydrofuran-2-carboxylic acid (3,4,6-Tri-O-benzoyl-2,5-anhydro-D-allonic acid, 2 g, 4 mmol) was dissolved in anhydrous THF (40 mL) under argon. Triphenylphosphine (2.1 g, 8 mmol) was then added, and the resulting mixture was stirred until it was completely dissolved. Subsequently 2,2'-dipyridyldisulfide (1.8 g, 8 mmol) was added to the reaction mixture. The mixture was stirred at room temperature for 2 hours, after which 3-methoxy-N-methylaniline (0.7 g, 5.6 mmol) was added and stirring was continued at room temperature for 16 hours. The solvent was evaporated to dryness, the residue was dissolved in chloroform (150 mL), the solution was washed twice with 0.1M NaOH solution (100 mL), twice with 0.2 M HCl solution (100 mL), once with saturated $NaHCO_3$ solution (100 mL), and dried ($Na_2SO_4$). The solution was evaporated to dryness and the residue dissolved in 7M solution of ammonia in methanol (250 mL). The solution was stirred for 16 hours at room temperature and evaporated to dryness. The residue was dissolved in chloroform and applied to a column of silica gel. Elution with a mixture of chloroform-methanol (3:1) and evaporation of the appropriate fractions yielded the title compound as a colorless oil (0.51 g, 1.7 mmol, 42%): MS (ES) m/z 399 [M+H+$C_6H_{15}N$]$^+$, 296 [M−H]$^−$.

Example 18

Preparation of ((2R,3S,4R)-3,4-dihydroxy-5-((3-methoxyphenyl)(methyl)carbamoyl)tetrahydrofuran-2-yl)methyltriphosphoric acid (Compound H)

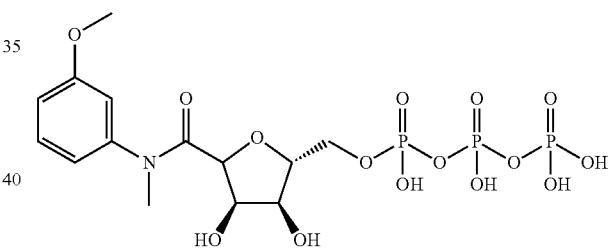

(3R,4S,5R)-3,4-Dihydroxy-5-(hydroxymethyl)-N-(3-methoxyphenyl)-N-methyltetrahydrofuran-2-carboxamide (N-(2,5-anhydro-D-allonoyl)-3-methoxy-N-methylaniline, 0.256 g, 0.86 mmol) was dissolved in 4 mL of trimethylphosphate under argon atmosphere. The solution was cooled to 0° C. and 0.35 mL of 2,6-lutidine was added. After 10 minutes, 0.14 mL (1.55 mmol) of phosphorous oxychloride was carefully added. Stirring was continued for 1 hour and then excess $POCl_3$ was removed in vacuo within 10 minutes. The remaining solution of the initially formed intermediate dichlorophosphate was then treated with a freshly prepared 1 M solution of tri-(n-butyl)-ammonium pyrophosphate (5.3 mL, 5.3 mmol) in DMF. After 2 minutes, the reaction was quenched by adding 50 mL of 0.25 M triethylammonium bicarbonate buffer (pH 7.5). Purification by ion exchange chromatography gave a crude product (95 mg) as a triethylammonium salt, which was subsequently purified by RP HPLC and precipitated as its sodium salt (52 mg, 0.1 mmol, 12%): $^1$H-NMR ($D_2O$): δ 3.23 (s, 3H, N—$CH_3$), 3.81 (s, 3H, O—$CH_3$), 3.95-4.20 (br m, 4H, H-3', H-4', H-5', H-5"), 4.27 (t, 1H, H-2'), 4.33 (d, 1H, H-1'), 6.94 (d, 1H, aromatic), 6.96 (s, 1H, aromatic), 7.02 (dd, 1H, aromatic), 7.40 (t, 1H, aromatic); MS (ES) m/z 536 [M−H]$^−$.

Example 19

Preparation of (3R,4S,5R)-3,4-dihydroxy-5-(hydroxymethyl)-N-(4-methoxyphenyl)-N-methyltetrahydrofuran-2-carboxamide

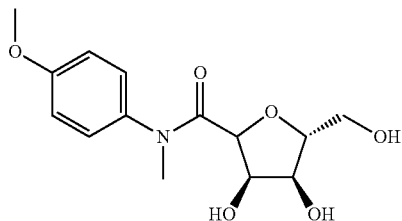 [SMILES: COc1ccc(N(C)C(=O)C2O[C@H](CO)[C@@H](O)[C@H]2O)cc1]

3,4,6-Tri-O-benzoyl-2,5-anhydro-D-allonic acid (2 g, 4 mmol) was dissolved in anhydrous THF (40 mL) under argon, and triphenylphosphine (2.1 g, 8 mmol) was added to the mixture. The resultant mixture was stirred until the triphenylphosphine was completely dissolved and subsequently 2,2'-dipyridyldisulfide (1.8 g, 8 mmol) was added. The mixture was stirred at room temperature for 2 hours, after which the 4-methoxy-N-methyl-aniline (0.768 g, 5.6 mmol) was added and stirring was continued at room temperature for 16 hours. The solvent was evaporated to dryness, the residue was dissolved in chloroform (150 mL) and washed twice with 0.1 M NaOH solution (100 mL), twice with 0.2 M HCl solution (100 mL), once with saturated NaHCO$_3$ solution (100 mL) and dried (Na$_2$SO$_4$). The solvent was evaporated to dryness and the residue was dissolved in 7M ammonia solution in methanol (250 ml) and stirred for 16 hours at room temperature and then evaporated to dryness. The residue was dissolved in chloroform and applied to a column of silica gel. Elution with a mixture of chloroform methanol (3:1) and evaporation of the appropriate fractions yielded the title compound as an off-white solid (0.77 g, 2.6 mmol, 65%): MS (ES) m/z 320 [M+Na]$^+$.

Example 20

Preparation of (2R,3S,4R)-2-(hydroxymethyl)-5-(((4-methoxyphenyl)(methyl)amino)methyl)tetrahydrofuran-3,4-diol

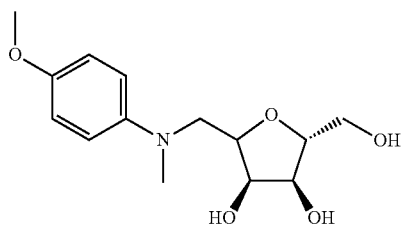 [SMILES: COc1ccc(N(C)CC2O[C@H](CO)[C@@H](O)[C@H]2O)cc1]

N-(2,5-anhydro-D-allonoyl)-4-methoxy-N-methyl-aniline (0.7 g, 2.4 mmol) was dissolved in anhydrous THF (80 mL) and the solution was cooled to 0° C. After 10 minutes, a lithium aluminium hydride solution (9.6 mL, 1M) in THF was added slowly over a period of 5 to 7 minutes and the resulting mixture was stirred for 1 hour. The reaction temperature was raised slowly from 0° C. to room temperature and stirring was continued for an additional 2 hours. The progress of the reaction was monitored by HPLC and the reaction was quenched carefully with water (300 mL) and adjusted to pH 7.5 with 1M HCl. The solids were separated by centrifugation and the residue was washed with water (2×50 mL). The combined solutions were evaporated in vacuo and the residue was treated with methanol (100 mL). The remaining solid was again separated by filtration and the filtrate was evaporated to dryness. The residue was purified by RP HPLC and evaporation of the appropriate fractions yielded the title compound as a yellow oil (170 mg, 0.6 mmol, 25%): MS (ES) m/z 284 [M+H]$^+$, 306 [M+Na]$^+$.

Example 21

Preparation of ((2R,3S,4R)-3,4-dihydroxy-5-(((4-methoxyphenyl)(methyl)amino)methyl)tetrahydrofuran-2-yl)methyltriphosphoric acid (Compound J)

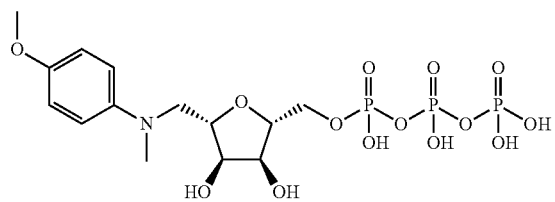 [SMILES: COc1ccc(N(C)C[C@@H]2O[C@H](COP(=O)(O)OP(=O)(O)OP(=O)(O)O)[C@@H](O)[C@H]2O)cc1]

(2R,3S,4R)-2-(Hydroxymethyl)-5-(((4-methoxyphenyl)(methyl)amino)methyl)tetrahydrofuran-3,4-diol (50 mg, 0.18 mmol) was dissolved in 3 mL of trimethylphosphate under argon atmosphere. The solution was cooled to 0° C. and after 10 minutes, 30 μL (0.3 mmol) of phosphorous oxychloride was added carefully. After 1 hour, excess POCl$_3$ was removed in vacuo over 10 minutes. The remaining solution of the initially formed intermediate dichlorophosphate was then treated with a freshly prepared 1 M solution of tri-(n-butyl)-ammonium pyrophosphate (0.9 mL, 0.9 mmol) in DMF. After 2 minutes, the reaction was quenched by adding 50 mL of 0.25 M triethylammonium bicarbonate buffer (pH 7.5). Purification by ion exchange chromatography gave a crude product (100 mg) as a triethylammonium salt, which was subsequently purified by RP HPLC and precipitated as its sodium salt (28 mg, 0.047 mmol, 26%): $^1$H-NMR (D$_2$O): δ 2.89 (s, 3H, N—CH$_3$), 3.70 (s, 3H, O—CH$_3$), 3.45-3.55 (br, m, 2H), 4.0-4.1 (br, m, 5H), 4.28 (t, 1H, H-1'), 6.97-7.05 (br, m, 4H, aromatic); MS (ES) m/z 522 [M−H]$^-$.

Example 22

((2R,3S,4R,5S)-3,4-Dihydroxy-5-((pyridin-3-ylamino)methyl)tetrahydrofuran-2-yl)methyltriphosphoric acid (Compound K)

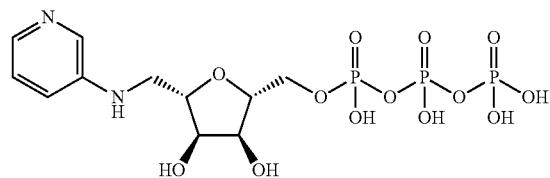 [SMILES: O=P(O)(O)OP(=O)(O)OP(=O)(O)OC[C@H]1O[C@@H](CNc2cccnc2)[C@H](O)[C@@H]1O]

The title compound was prepared by following the procedure described for Example 21 (Compound J). $^1$H-NMR ($D_2O$): δ 2.89 (s, 3H, N—$CH_3$), 3.70 (s, 3H, O—$CH_3$), 3.35-3.55 (m, 2H), 4.0-4.1 (m, 4H), 4.15 (t, 1H), 4.25 (t, 1H), 6.95-7.10 (br, m, 2H, aromatic), 7.90 (br S, 1H), 8.25 (br S, 1H); MS (ES) m/z 479.2 $[M-H]^-$.

Example 23

Preparation of 3-Hydroxypyridine, silver salt

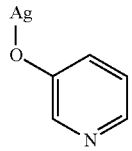

All operations were performed in a dark fume hood. Silver nitrate (1.7 g, 10 mmol) was dissolved in 8 mL water and added to a solution of 3-hydroxypyridine (951 mg, 10 mmol) in 20 mL of aqueous sodium hydroxide (400 mg, 10 mmol) solution. The resulting precipitate was filtered, washed with water, ethanol, and then diethyl ether. The solid was dried under vacuum to yield the title compound as a brown powder (2.0 g, 9.9 mmol, 99%).

Example 24

Preparation of 3-Pyridyl 2,3,5-tri-O-benzoyl-β-D-ribofuranoside

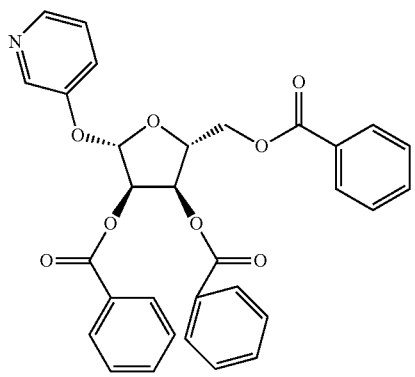 [SMILES: O=C(OC[C@H]1O[C@@H](Oc2cccnc2)[C@H](OC(=O)c2ccccc2)[C@@H]1OC(=O)c1ccccc1)c1ccccc1]

2,3,5-Tri-o-benzoyl β-D-ribofuranosyl chloride (2.3 g, 4.8 mmol) was azeotropically dried with toluene (2×20 mL), re-dissolved in 20 mL of dry toluene and added to an azeotropically dried (2×20 mL toluene) suspension of 3-hydroxypyridine silver salt (1.95 g, 9.55 mmol) in 200 mL toluene and refluxed under argon for 48 hours. The mixture was cooled to room temperature, filtered, and the solution was evaporated to dryness in vacuo. The residue was then dissolved in toluene (100 mL) and purified by chromatography on silica gel (eluting, starting with pure toluene, then a mixture of toluene-acetonitrile 100:3 and finally pure methanol) to yield the title compound as black gum (0.92 g, 1.7 mmol, 35%).

Example 25

Preparation of 3-Pyridyl-β-D-ribofuranoside

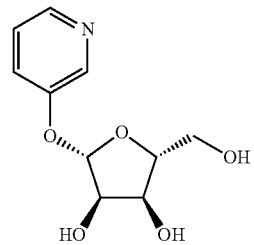 [SMILES: OC[C@H]1O[C@@H](Oc2cccnc2)[C@H](O)[C@@H]1O]

In a pressure bottle (Sigma-Aldrich), 3-pyridyl 2,3,5-tri-O-benzoyl-β-D-ribofuranoside (0.92 g, 1.7 mmol) was dissolved in 50 mL of an ammonia solution (33%) in water. The solution was stirred for 20 hours at 60° C. The solution was evaporated to dryness. The residue was dissolved in 80 mL chloroform-acetonitrile (3:1) and applied to a column of silica gel. Elution with a mixture of $CHCl_3$—$CH_3CN$ (3:1) and evaporation of the appropriate fractions yielded the crude product (0.3 g) which was purified by preparative RP-HPLC to yield the title compound (0.25 g, 1.3 mmol, 76%): MS (ES) m/z 250 $[M+Na]^+$.

Example 26

Preparation of 3-Pyridyl-β-D-ribofuranoside-5'-triphosphate (Compound M)

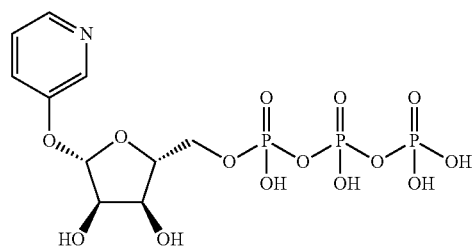 [SMILES: O=P(O)(O)OP(=O)(O)OP(=O)(O)OC[C@H]1O[C@@H](Oc2cccnc2)[C@H](O)[C@@H]1O]

3-Pyridyl-β-D-ribofuranoside (0.97 g, 0.43 mmol) was dissolved in 5 mL of trimethylphosphate under an argon atmosphere. The solution was cooled to 0° C. and 0.17 mL of 2,6-lutidine was added. After 10 minutes, 70.1 µL (0.77 mmol) of phosphorous oxychloride was carefully added. After 1 hour, excess of $POCl_3$ was removed in vacuo over 10 minutes. The remaining solution of the initially formed intermediate dichlorophosphate was then treated with a freshly prepared 1 M solution of tri-(n-butyl)-ammonium pyrophosphate (2.1 mL, 2.1 mmol) in DMF. After 2 minutes, the reaction was quenched by adding 50 mL of 0.25 M triethylammonium bicarbonate buffer (pH 7.5). Purification by ion exchange chromatography gave a crude product (108 mg) as a triethylammonium salt, which was subsequently purified by RP HPLC and precipitated as its sodium salt (50 mg, 0.09 mmol, 21%): $^1$H-NMR ($D_2O$): δ 4.07-4.14 (m, 2H, H-5', H-5"), 4.30 (m, 1H, H-4'), 4.39 (m, 1H, H-3'), 4.55 (m, 1H, H-2'), 5.70 (br, s, 1H, H-1'), 7.45 (m, 1H, aromatic), 7.61 (br, d, 1H, aromatic), 8.23 (br, s, 1H, aromatic), 8.34 (br, s, 1H, aromatic); MS (ES) m/z 466 $[M-H]^-$.

Example 27

Preparation of Compound N

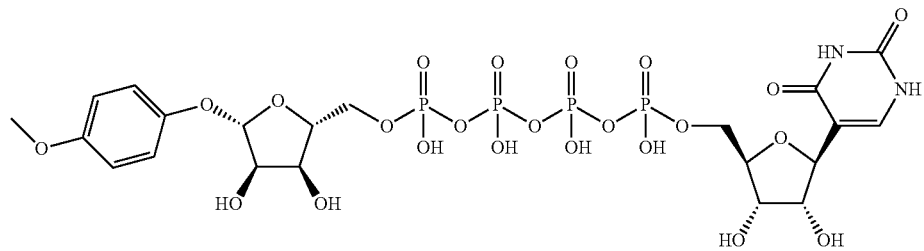 [SMILES: COc1ccc(O[C@@H]2O[C@H](COP(=O)(O)OP(=O)(O)OP(=O)(O)OP(=O)(O)OC[C@H]3O[C@@H](c4c[nH]c(=O)[nH]c4=O)[C@H](O)[C@@H]3O)[C@@H](O)[C@H]2O)cc1]

4-Methoxyphenyl-β-D-ribofuranoside-5'-triphosphate sodium salt (131 mg, 0.23 mmol) was dissolved in water (0.5 ml), and $MnCl_2 \times 2H_2O$ (186 mg, 1.15 mmol) was added. Subsequently a solution of pseudouridine-5'-phosphorimidazolate (442 mg, 1.15 mmol) in 0.2 M N-ethylmorpholine-HCl buffer pH 7.0 (3 ml) was added. The pH of the resulting suspension was adjusted carefully from 2.0 to 6.0 with 2 M NaOH solution. The suspension was stirred for 3 days at room temperature. The reaction mixture was then treated with a 1 M versenol solution until the suspension became clear. Subsequently, it was diluted to 2000 mL, the pH was adjusted to 7.5, and the solution was passed through ion exchange chromatography column. The fractions containing the product was subsequently purified by RP HPLC chromatography. The title product was precipitated as its sodium salt (12 mg, 0.013 mmol, 6%): $^1$H-NMR ($D_2O$): δ 3.65 (s, 3H), 3.90-4.50 (m, 11H), 5.34 (s, 1H), 6.80 (d, 2H), 6.90 (d, 2H), 7.60 (s, 1H); MS (ES): m/z 801 [M−H]$^+$.

Example 28

Preparation of 1-Methyl-Adenosine-5'-triphosphate (Compound P)

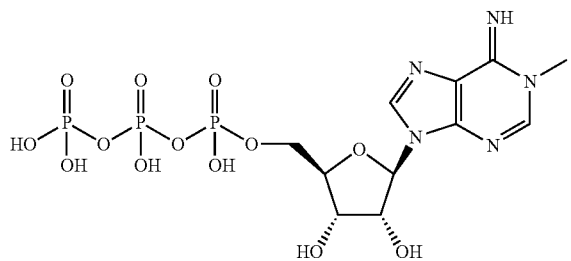 [SMILES: Cn1cnc2c(ncn2[C@@H]2O[C@H](COP(=O)(O)OP(=O)(O)OP(=O)(O)O)[C@@H](O)[C@H]2O)c1=N]

Adenosine-5'-triphosphate sodium salt (10 g, 17.6 mmol) was dissolved in water (50 mL). The solution was applied to a Dowex 50WX8 column (200 mL) in the pyridinium form. Subsequently the column was washed with 600 mL water-methanol (1:1). The elute was directly caught in a cold stirred solution of tri-n-butylamine (37.7 mL, 158.4 mmol) in methanol. The solution was evaporated to dryness, dissolved in methanol and re-evaporated twice. Next, this procedure was repeated twice with anhydrous DMF (700 mL) on an oil pump. The residue was dissolved in 700 ml anhydrous DMF. Then, iodomethane (17.5 mL, 281 mmol) was added and the reaction mixture was stirred at room temperature for 20 h. The solution was evaporated to dryness, the residue was dissolved in water (1000 mL) and the pH of the solution was adjusted from 1.2 to 7.5 with 1M triethylammonium bicarbonate (pH 11.0). Purification by ion exchange chromatography in two 5 mmol batches yielded the crude product as a triethylammonium salt. The title product was precipitated as its sodium salt (0.44 mmol, 18%).: $^1$H-NMR ($D_2O$): δ 3.75 (s, 3H, N1-CH$_3$), 4.00-4.20 (br m, 2H, H-5', H-5"), 4.24 (m, 1H, H-4'), 4.45 (m, 1H, H-3'), 4.65 (m, 1H, H-2'), 6.00 (d, 1H, H-1'), 8.35 (s, 1H, heterocyclic), 8.50 (s, 1H, heterocyclic); MS (ES) m/z 521.9 [M+H]$^+$.

Example 29

The compounds described herein may be tested for their ability to elicit P2Y$_2$ receptor activity using in vitro IP1 accumulation, intracellular calcium mobilization, mucus production and ciliary beat frequency assays, ex vivo Short Current Circuit and fluid transport assays for P2Y$_2$ and other P2Y receptor activity assays, as described below.

Cell-Based Assays:

Intracellular Calcium Mobilization Assays and Chloride Measurements:

Epithelial cells from the gastrointestinal tract or otherwise or P2Y2 stably expressing transfected cells are grown overnight to confluency. The day before the experiment, cells in midlog phase are detached with PBS-EDTA and resuspended in media without antibiotics at $2.5 \times 10^5$ cells/mL. Cells (100 µL) are then distributed into a 96 well plate (Perkin Elmer, #6005182) and the plate is incubated overnight in a cell culture incubator. The next morning, the media is drained and 100 µL of Dye solution (5 µM Fluo-4 AM, 2.5 mM Probenicid, 1 mg/mL Pluronic acid, 0.1% BSA, 135 mM NaCl, 5 mM KCl, 1.8 mM CaCl$_2$, 1 mM MgCl$_2$, 10 mM HEPES, 5.6 mM Glucose, 0.05% Gelatin, pH 7.4) are added. The plate is then incubated for 1 hour at 37° C. in a cell culture incubator. The media is drained and the wells washed twice with buffer A (2.5 mM Probenicid, 1 mg/ml Pluronic acid, 0.1% BSA, 0.05% Gelatin, 135 mM, NaCl, 5 mM KCl, 1.8 mM CaCl$_2$, 1 mM MgCl$_2$, 10 mM HEPES, 5.6 mM Glucose, pH 7.4). The wells are filled with 50 µL of buffer A and the plate is incubated for 20 min. at room temperature in the dark (for the apyrase assays, apyrase is added during this step at a final concentration of 10 Units/mL. The agonists are diluted in buffer A and injected with the injection system of the reading machine (FDSS6000. from Hamamatsu Photonics). Fluorescence changes are recorded over 180 sec. and dose-response curves are generated by plotting the ligand concentrations versus the ratio signal/noise.

IP$_1$ Accumulation Assay (Kit IP-One HTRF)

Cells in midlog phase are collected with PBS-EDTA, washed and resuspended in medium without antibiotics at a concentration of $2\times10^5$ cells/ml. Cells (200 µL or 40.000 cells) are then distributed into a 96 well plate (Cellstar, Greiner, 655083). The plate is incubated overnight at 37° C. in a cell culture incubator. The next morning, the medium is removed and replaced by 50 µL of agonist diluted in the stimulation buffer provided with the kit IP-one (CisBio, 621P1PEB). The plate is incubated for 1 h at 37° C. in a cell culture incubator. 25 µL of the antibody diluted in lysis buffer is then added to each well. 25 µL of the IP1-d2 diluted in lysis buffer is added to each well and the plate is incubated for 1 h. at room temperature. The plate is then read on a Rubystar and dose-response curves are generated by plotting the ligand concentrations versus the DeltaF ratio.

Mucus Production Detection Assays:

Increase in the mucus secretion from the luminal surface of epithelial preparations is determined by the increase in the periodic-acid and Schiff's (PAS) reagent staining. P2Y2 induced increase in the mucus secretion was also verified by (Enzyme Linked Immunoabsorbent Assay) ELISA assays using mucin specific antibodies. Alternatively, primary tracheal, bronchial or gastrointestinal epithelial cells are cultured in epithelial growth medium (Clonetics, CC-3170 BEGM bullet kit base media in addition to other supplements). Upon exposure to a P2Y2 agonist, the mucin production is detected by ELISA.

Ciliary Beat Frequency Assays:

The effects of an P2Y2 agonist on ciliary activity can be determined on individual human ciliated nasal epithelial cells using techniques described by Geary et al., 1995; and Morse et al., 2001. Briefly, epithelial cells are recovered from protease digests of human nasal turbinates procured through the Tissue Culture Core Facility of the Cystic Fibrosis/Pulmonary Research and Treatment Center at the University of North Carolina at Chapel Hill. The cells are seeded into 12-mm Costar Transwell-Col cell culture supports at a density of 300,000 cells/cm$^2$ and incubated overnight in hormone-supplemented culture medium (Gray et al., 1996) at 37° C. in an atmosphere of air (5% $CO_2$), after which nonadherent cells are washed away to reveal small explants of the superficial epithelium as small clumps of ciliated cells that had attached to the substratum. These preparations are used within 4 days. Transwell-Col cell culture supports bearing epithelial explants are mounted in a chamber on the stage of an inverted microscope, superfused luminally, and warmed (35 degree Celsius) as described previously by Morse et al., 2001. The control superfusion and the serosal bathing solution is Krebs-Ringer bicarbonate (KRB) with the following composition: 125 mM NaCl, 5.2 mM KCl, 1.2 mM $MgCl_2$, 1.2 mM $CaCl_2$, 25 mM $NaHCO_3$, 10 mM TES, 5 mM glucose (pH 7.4 when gassed with 5% $CO_2$). The explanted, native ciliated cells are viewed by phase contrast microscopy using a Zeiss IM microscope (Carl Zeiss Inc., Thornwood, N.Y.) and 32-objective, and the image is monitored with a Dage 72 monochrome charge-coupled device video camera (Dage-MTI, Michigan City, Ind.). Ciliary beat frequency (CBF) is determined using a photosensor positioned over the image of an individual cell on the face of the video monitor to detect ciliary beating, as previously described by Morse et al., 2001. In all experiments, cultures are equilibrated with 1.5 h of superfusion with KRB. Each preparation is then subjected to two 10-min. baseline and agonist stimulation periods, first with a variable concentration of the agonist compound, then with 100 µM UTP as the agonist, with data recorded every minute for the determination of CBF. A 30-min. KRB washout period separates the agonist challenge from the second baseline period. After fast Fourier transformation analyses for each experiment, the resulting CBF data are normalized to the respective mean baseline.

Conjunctival Preparations and Short Circuit Current $I_{sc}$ Assays:

Designated rabbits are euthanized with pentobarbital sodium solution. The eyes including eyelids are enucleated immediately along the superior and inferior orbit. Only freshly dissected preparations are used, and this entails that only one of the eyes of a given rabbit are used for each experiment. The eyeball is placed on a semispherical Lucite holder, where it is secured in place by vacuum. The eyelids are then pulled up, which results in extending the conjunctiva, forming a cylinder. The eyelids are sutured to a circular holder held on a manipulator. The holder is adjusted to maintain the conjunctiva in cylindrical shape, with the epithelium covering the internal surface. The inside of the conjunctival cylinder is filled with prewarmed (37° C.) Tyrode solution, and the subconjunctival tissues and extraocular muscles are trimmed off the outside. The conjunctival cylinder is then cut open from one of the canthi to the corneal limbus vertically, followed by cutting all along the limbus. At this point, the entire conjunctiva thus obtained, including the free bulbar and fornix sections plus the palpebral conjunctiva still attached to the eyelids, is placed into a dish with Tyrode solution at 37° C. and gassed with air-5% $CO_2$. With the help of a dissection microscope, the palpebral conjunctiva is dissected off the eyelids, which yields the whole conjunctiva isolated in one piece. These $I_{sc}$ measurements are done with an Using system [World Precision Instruments (WPI), Sarasota, Fla.]. The isolated rabbit conjunctival epithelium preparation is clamped in a model CHM2 WPI chamber. The solutions are bubbled with air-5% $CO_2$ and maintained at 37° C., using the thermally jacketed glass lifts of the system. The $I_{sc}$ across the tissue is measured using a four-electrode WPI DVC 1000 voltage-current clamp.

Fluid Transport Assays:

Isolated rabbit conjunctival or gastrointestinal epithelial preparations are mounted in an insert made of two flat Lucite rings, one of them having a stainless steel mesh to support the tissue. The insert is clamped between two thermally jacketed fluid-filled chambers (37° C.). The mucosal side (top) chamber is stoppered and is in contact with the outside through a narrow piece of tubing (to minimize evaporation); the serosal (bottom) chamber is closed except for the detector, also enclosed to minimize evaporation. The rate of fluid traversing the preparation is determined by keeping constant the volume of the stromal side chamber. The microelectrode contact detector used is triggered by volume variations of 1-3 nL; to avoid its blockage, voltage to it is limited to 100 mV. The nanoinjector voltage output is proportional to the volume injected or (withdrawn) by the syringe in each cycle; such output goes to a pen-chart recorder and to a computer in oscillograph mode. To function, the method requires the tissue to be applied against its support by a pressure head. In addition, if that pressure head is 1.5 cm $H_2O$, capillarity artifacts at the detector are possible. The relative positions of chamber and detector are therefore such that the hydrostatic pressure difference (mucosa minus stroma) across the conjunctival preparation is 3.0 cm $H_2O$.

$EC_{50}$ values for certain compounds were obtained through an IP1 accumulation assay (kit IP-one HTRF), as described above. The data is provided in the following Table.

| Compound | +++ (<500 nM) | ++ (500-1000 nM) | + (>1000 nM) |
|---|---|---|---|
| Compound C | X | | |
| Compound D | X | | |
| Compound E | | | X |
| Compound J | | | X |
| Compound K | | | X |
| Compound M | | | X |
| Compound N | | X | |
| Compound P | X | | |

Example 30

The compounds described herein may be tested for their ability to increase intestinal transit and thus to treat constipation, as described below.

Part I: Compound C Increases Intestinal Transit in Mice, Measured as Time to First Red Pellet.

The effect of compound C on total GI transit was measured in mouse and compared to vehicle in order to demonstrate that the compound increases the rate of gastrointestinal (GI) transit. Briefly, mice were administered a meal containing a non-absorbable red dye (carmine) and were monitored for 3 hours. Feces were collected and time of expulsion was recorded. Feces were weighed fresh and again after overnight drying. Time to first red-colored feces was used as a measure of total GI transit time. Total weight of wet and dry feces was used as a measure of fluid secretion.

Male Balb/C mice were fasted overnight with free access to water. They were then given access to food and water for 30 minutes. They were finally moved to empty plastic cages with no access to food or water. After 1 hour, each mouse was fed a liquid meal of 0.5% methylcellulose (weight-to-volume w/v) in water containing 3% carmine dye (w/v) as well as doses of the test compound at 5 and 50 mg/kg (10 mL/kg) with a gavage needle. Control animals received vehicle only. Each animal was held in an individual cage for the following 3 hours. The expulsion time of each feces was recorded to the nearest 5 seconds. Each feces was placed in a tared vial and the vial was capped. Fresh feces were weighed and the vials were kept uncapped overnight at 37° C. The feces were then weighed again. Average times to first red-colored feces for vehicle- and compound-dosed animals were compared using a Student's t-test (two-sided, unequal variance). A P-value of 0.05 or less was considered statistically significant. A similar comparison was made for total weight of fresh feces, dry feces, and water content using a one-way ANOVA with Dunnett post-test. A P-value of 0.05 was considered statistically significant.

Figure 2:
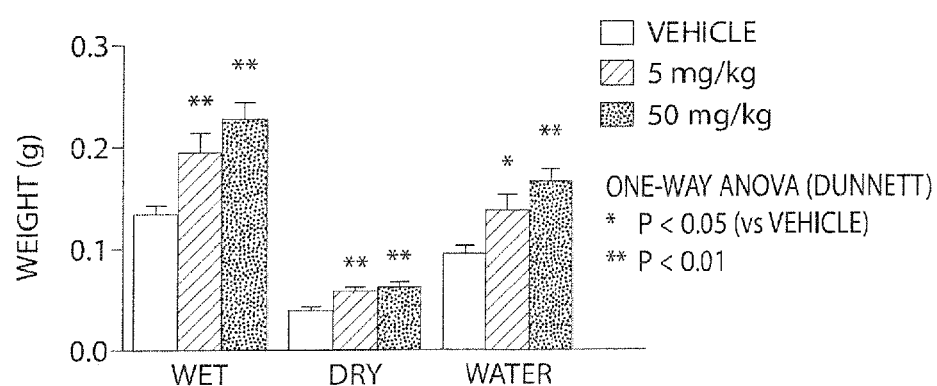
FIG. 2 depicts the results of an assay measuring the weight of feces 3 hours after administering a dose of compound C to male Balb/C mice. The graph illustrates the total weight of feces (wet, dry), and water content produced 3 hrs after dosing, as a function of the dose of compound C (N=18 animals for vehicle, 7 for 5 mg/kg, and 8 for 50 mg/kg).

As seen in FIGS. 1 and 2, compound C dose-dependently increases GI transit since time to first red pellet decreases with increasing dose. Examination of the total weight of feces produced during 3 hours, as described in the protocol above, shows a dose-dependent increase in wet, and dry feces, as well as in water content.

Part II: Compound C Increases Colonic Transit in Mice.

In order to further probe the mechanism of action of Compound C on gastrointestinal (GI) transit, the effect of the compound on stomach, small intestine, and large intestine transit time was measured in two separate experiments.

Gastric Retention and Small Intestine Transit.

Figure 3:
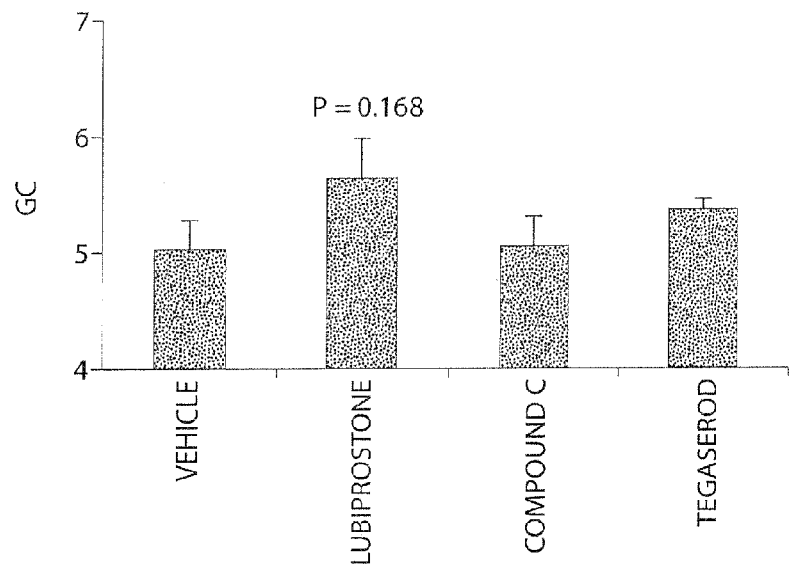
FIG. 3 depicts the results of a study using male Balb/C mice. The graph depicts the geometric center (GC) of the small intestine of the mice 30 min. after administering a Tc-sulfur colloid meal. The results are for animals dosed ip with tegaserod (0.1 mg/kg), and animals dosed orally with lubiprostone (0.1 mg/kg) or compound C (50 mg/kg). No statistical significance was observed using the 1-way ANOVA or Student's t-test.
Figure 4:
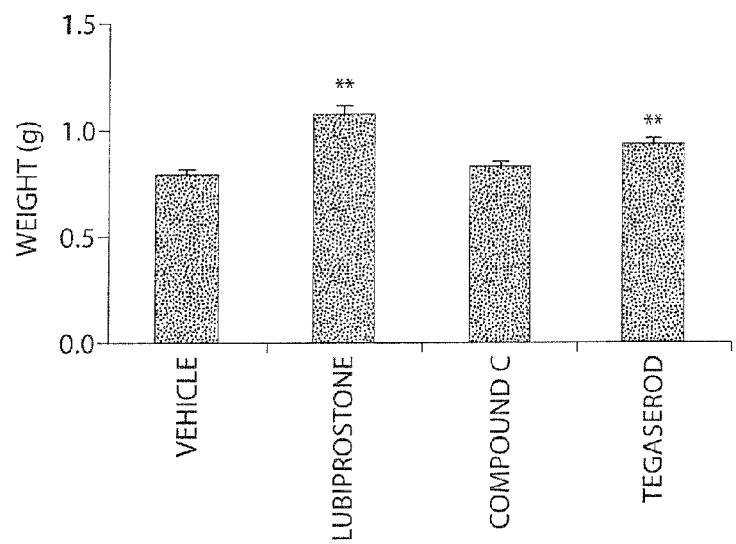
FIG. 4 depicts the results of a study using male Balb/C mice. The graph depicts the sum of weights of the sections of small intestine of the mice 30 min. after administering a Tc-sulfur colloid meal. The results are for animals dosed ip with tegaserod (0.1 mg/kg), and animals dosed orally with lubiprostone (0.1 mg/kg) or compound C (50 mg/kg). (** indicates statistically significance, P<0.05, 1-way ANOVA with Dunnett post-test against vehicle)
Figure 5:
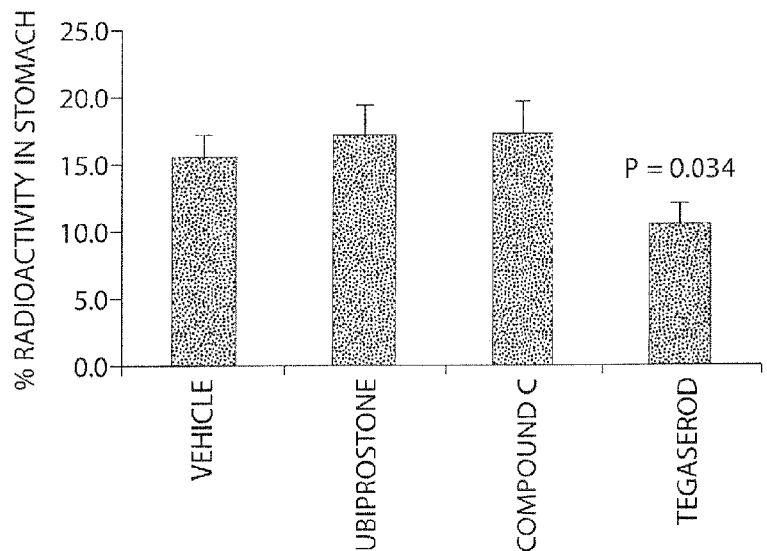
FIG. 5 depicts the results of an assay measuring stomach retention expressed as a percentage of the total radioactivity left in the stomach of male Balb/C mice 30 min. after administering a Tc-sulfur colloid meal. The results are for animals dosed ip with tegaserod (0.1 mg/kg), and animals dosed orally with lubiprostone (0.1 mg/kg) or compound C (50 mg/kg). No statistical significance was found using 1-way ANOVA, but there was statistically significance for tegaserod versus vehicle using Student's t-test.
Figure 6:
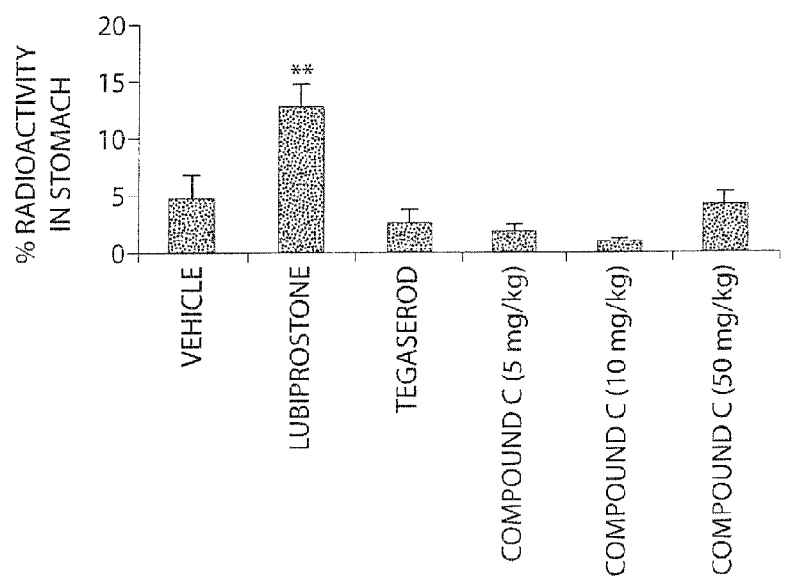
FIG. 6 depicts the results of an assay measuring the percentage of total radioactivity left in stomach of male Balb/C mice 2.5 hr after administering a Tc-sulfur colloid meal. The results are for animals dosed ip with tegaserod (0.1 mg/kg), and animals dosed orally with lubiprostone (0.1 mg/kg) or compound C. (** indicates statistically significance, P<0.05, 1-way ANOVA with Dunnett post-test against vehicle.)
Figure 7:
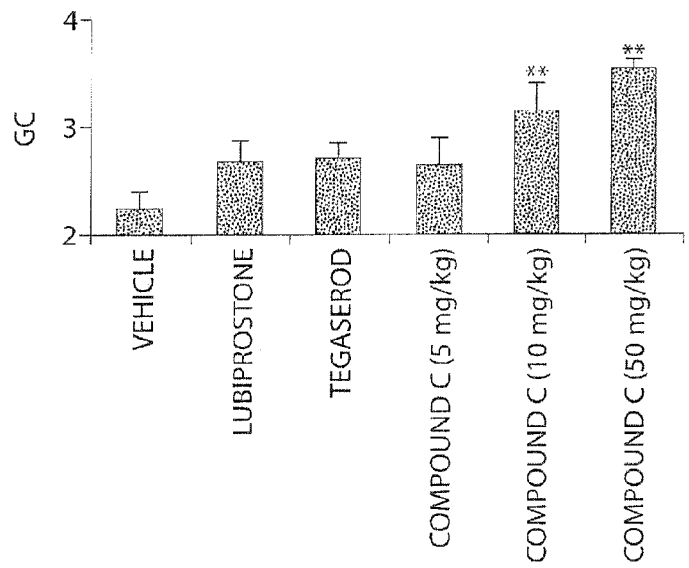
FIG. 7 depicts the results of an assay measuring the geometric center (GC) of the large intestine and feces of male Balb/C mice 2.5 hr after administering a Tc-sulfur colloid meal. The results are for animals dosed ip with tegaserod (0.1 mg/kg), and for animals dosed orally with lubiprostone (0.1 mg/kg) or compound C. (** indicates statistically significance, P<0.05, 1-way ANOVA with Dunnett post-test against vehicle.)
Figure 8:
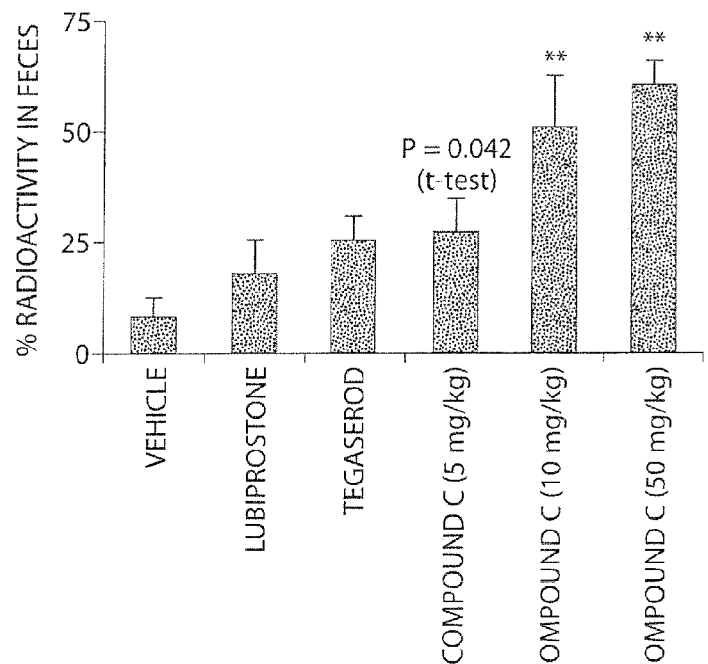
FIG. 8 depicts the results of an assay measuring the percentage of total radioactivity found in the feces of male Balb/C mice 2.5 hr after administering a Tc-sulfur colloid meal. The results are for animals dosed ip with tegaserod (0.1 mg/kg), and animals dosed orally with lubiprostone (0.1 mg/kg) or compound C. (** indicates statistically significance, P<0.05, 1-way ANOVA with Dunnett post-test against vehicle.)
Figure 9:
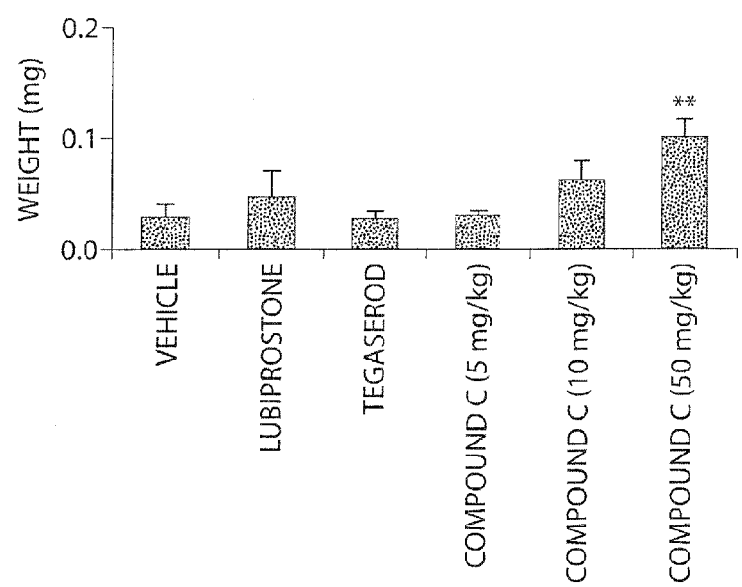
FIG. 9 depicts the results of an assay measuring the total weight of feces of male Balb/C mice 2.5 hr after administering a Tc-sulfur colloid meal. The results are for animals dosed ip with tegaserod (0.1 mg/kg), and for animals dosed orally with lubiprostone (0.1 mg/kg) or compound C. (** indicates statistically significance, P<0.05, 1-way ANOVA with Dunnett post-test against vehicle.)

Male Balb/C mice were fasted overnight with free access to water. Water was then removed for 30 minutes. Each mouse was subsequently gavaged a liquid meal of 0.5% methylcellulose (weight-to-volume w/v) and 10% corn oil (volume-to-volume v/v) in water containing 5-10 µCi of an non-absorbable Tc-sulfur colloid radioactive marker as well as compound C at doses between 2 and 50 mg/kg (10 mL/kg), or lubiprostone at 100 µg/kg. A group was dosed with tegaserod (100 µg/kg) injected ip just prior to receiving vehicle by oral gavage. Control animals received vehicle only. Animals were euthanized 30 minutes after dosing and their GI tract was excised from the stomach down. The stomach was counted alone. The small intestine was extended and cut into 10 equally sized pieces, labeled 1 to 10 from stomach to caecum. Each piece of the small intestine, and the stomach, were counted for radioactivity. The geometric center (GC) of the small intestine was calculated according to $GC=(\Sigma(i \times C_i))/(\Sigma C_i)$, where i is the label of the segment (from 1 to 10) and $C_i$ is the number of counts. GC is a number between 1 and 10. The closer GC is to 10, the faster the small intestinal transit. Gastric retention was calculated as percent of total dose counted. GC's and gastric retentions were compared between dose and vehicle groups using a Student's t-test. A P-value of less than 0.05 was considered statistically significant, as depicted in FIGS. 3-5.

Large Intestine Transit.

Male Balb/C mice were fasted overnight with free access to water. Water was then removed for 30 min. Each mouse was subsequently gavaged a liquid meal of 0.5% methylcellulose (weight-to-volume w/v) and 10% corn oil (volume-to-volume v/v) in water containing 5-10 µCi of an non-absorbable Tc-sulfur colloid radioactive marker containing the compound C at doses of 5, 10 and 50 mg/kg (10 mL/kg), or lubiprostone at 100 µg/kg. A group was dosed with tegaserod (100 µg/kg) injected ip just prior to receiving vehicle by oral gavage. Control animals received vehicle only. Animals were kept for 30 minutes in empty cages then given access to food and water at libitum. They were euthanized 2.5 hours after dosing and their GI tract was excised from the stomach down. The stomach and small intestine were counted alone. The large intestine was extended and cut into 3 equally sized pieces, labeled 1 to 3 from caecum to rectum. Each section was counted individually. Feces, labeled 4, were collected, weighed, and counted. The geometric center (GC) of the large intestine/feces portion of the GI tract was calculated according to $GC=(\Sigma(i \times C_i))/(\Sigma C_i)$, where i is the label of the segment (from 1 to 4) and $C_i$ is the number of counts. GC is a number between 1 and 4. The closer GC is to 4, the faster the intestinal transit. Between 7 and 12 mice were used for each dose group. Gastric retention was calculated as percent of total dose counted. Gastric retentions between compound-dosed and vehicle-dosed animals were compared using a one-way ANOVA test and a Dunnett post-test. GC's and feces weights were compared between compound- and vehicle-dosed animals using a similar statistical methodology. In all cases, a P-value of less than 0.05 was considered statistically significant.

As seen in the FIGS. 6-9, compound C dose-dependently increases GI transit since the calculated large intestine geometric center increases with increasing dose. Compound C appears to have a statistically significant effect at 10 mg/kg dose and higher. The effect observed at a dose of 5 mg/kg is equivalent to that obtained with doses of lubiprostone (0.1 mg/kg) and tegaserod (0.1 mg/kg) previously established as being efficacious. The same dose-dependent efficacy is observed in a dose-dependent increase of % total radioactivity starting at 5 mg/kg dose at a percentage equivalent to that obtained with lubiprostone and tegaserod. A similar conclusion can be made from the total weight of feces. Finally, compound C appears to have virtually no effect on gastric retention at doses up to 50 mg/kg, unlike lubiprostone that appears responsible for a significant delay in gastric emptying.

Part III: Stability of Compound C in Rat Intestinal Fluids.

The stability of a compound, e.g., compound C, in the gastrointestinal (GI) tract can be determined by dissolving the compound in rat GI fluids and evaluating the composition of the result mixture by an LC-MS method. The half-life of the compound can be determined by fitting the data to an exponential decay model.

For example, compound C is dissolved in PBS at ~100 μM. Rat intestinal fluids (jejunum and colon) can be obtained from Bioreclamation, Inc. (Hicksville, N.Y.). The stability of compound C can also be assessed at low pH (pH=3.2; 0.1M glycine buffer). Both stock solution and rat fluids are incubated at 37° C. for ~30 minutes prior to initiating the study. After ~30 minutes, 10 μL aliquot of compound C stock solution is added to 100 μL of intestinal fluid. The mixture is briefly vortexed and sampled right away for LC/MS analysis (Chromasil C18, 4.6×50 mm; solvent A: 20 mM acetic acid, 0.025% v/v dimethylhexylamine, pH=7.4 adjusted with ammonium hydroxide, 5% v/v methanol; solvent B: 70% methanol, 30% solvent A v/v; 0.8 mL/min; gradient from 2% to 60% B then 60 to 95% B and back to 2%; detection by electrospray in single ion mode at M-1 or 838.4 a.m.u.). The mixture can be automatically sampled and analyzed every 5 to 15 minutes. Chromatograms are integrated, and peak area vs time are plotted and fitted to a monoexponential decay curve. Stability can be reported as half-life, $t_{1/2}$ (in hr).

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference for all purposes. The appropriate components, processes, and methods of those patents, applications and other documents may be selected for the invention and embodiments thereof.

We claim:
1. A compound of formula IA:

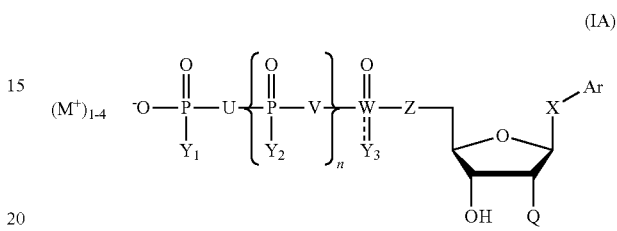

or enantiomers, diastereomers, enantiomerically enriched mixtures, racemic mixtures, crystalline forms, non-crystalline forms, amorphous forms, or pharmaceutically acceptable salts thereof, wherein:

Ar is an aryl, alkyl, cycloalkyl, aralkyl, or a heteroaryl or fused heteroaryl group containing 1-4 heteroatoms; each of which is optionally substituted with one or more of a halo, hydroxy, alkyl, alkoxy, carboxy, cyano, nitro, sulfonamido, sulfonate, amino, imino, alkylamino, or dialkylamino group or groups; provided that when X is O, Ar is neither unsubstituted phenyl, anilino, nor 4-nitrophenyl;

X is a bond or is selected from the group consisting of O, S, S(O), S(O$_2$), N(R'), —C(O)N(R')—, and —(CH$_2$)$_m$X$^1$—;

X$^1$ is O, S, S(O), S(O$_2$), or N(R');

R' is H, alkyl, or aralkyl;

Q is selected from the group consisting of H; OH; lower alkoxy; halo; mono-, di- or trihalomethyl; amino; lower alkylamino; and lower dialkylamino group;

U and V each represent independently for each occurrence O; NH; a lower alkylamino diradical; methylene; or mono- or dihalomethylene;

Y$_1$, Y$_2$, and Y$_3$ each represent independently for each occurrence O, O$^-$;

S$^-$; or substituted or unsubstituted lower alkoxy, aryloxy, aralkyloxy, or cycloalkyloxy groups;

Z is O, NH, or a lower alkylamino diradical;

m and n are independently 0, 1 or 2;

W is P and

M is H or a salt-forming cation.

2. A compound of formula IIA:

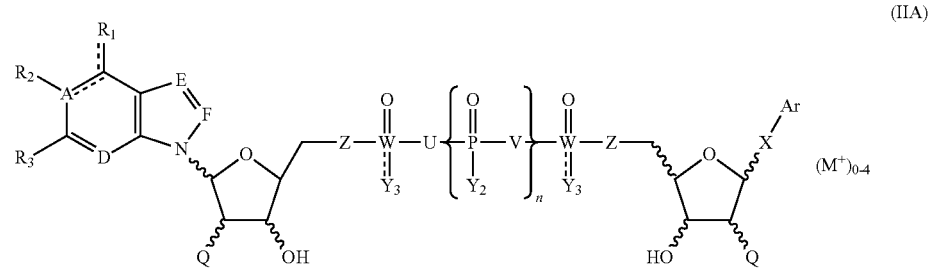

or enantiomers, diastereomers, enantiomerically enriched mixtures, racemic mixtures, crystalline forms, non-crystalline forms, amorphous forms, or pharmaceutically acceptable salts thereof, wherein:

A, D, and E are independently N, C($R_5$), or CH;

F is N or C($R_4$);

$R_1$ is an H, oxo, lower alkoxy, lower alkylamino, lower dialkylamino, imino, lower alkyl-substituted imino, lower thioalkyl, aryl, substituted or unsubstituted lower alkyl, or lower alkyl-substituted aryl group;

$R_2$ is absent or is selected from the group consisting of a lower alkyl, lower alkoxy, lower alkyl-substituted aryl, aralkyl, and cycloalkyl group;

$R_3$ and $R_4$ are independently an H, lower thioalkyl, substituted lower alkyl, or unsubstituted lower alkyl group;

$R_5$ is a lower alkyl, lower alkoxy, lower alkyl-substituted aryl, aralkyl, or cycloalkyl group;

Ar is an aryl, alkyl, cycloalkyl, arylalkyl, or a heteroaryl or fused heteroaryl group containing 1-4 heteroatoms; each of which is optionally substituted with one or more of a halo, hydroxy, alkyl, alkoxy, carboxy, cyano, nitro, sulfonamido, sulfonate, amino, alkylamino, or di-alkylamino group or groups; provided that when X is O, Ar is neither unsubstituted phenyl, anilino, nor 4-nitrophenyl;

X is a bond or is selected from the group consisting of O, S, S(O), S($O_2$), N(R'), —C(O)N(R')—, and —($CH_2$)$_m$ $X^1$—;

$X^1$ is O, S, S(O), S($O_2$), or N(R');

R' is H, alkyl, or aralkyl;

Q represents independently for each occurrence an H; OH; lower alkoxy; halo; mono-, di- or trihalomethyl; amino; lower alkylamino, or lower dialkylamino group;

U and V each represent independently for each occurrence O; NH; a lower alkylamino diradical; methylene; or mono- or dihalomethylene;

$Y_2$ and $Y_3$ each represent independently for each occurrence O, $O^-$; $S^-$; or a substituted or unsubstituted lower alkoxy, aryloxy, aralkyloxy, or cycloalkyloxy group;

M is H or a salt-forming cation;

Z represents independently for each occurrence O, NH, or a lower alkylamino diradical;

m and n are independently 0, 1 or 2; and

W is P.

3. The compound of claim 2, which is a compound of formula IIA-1:

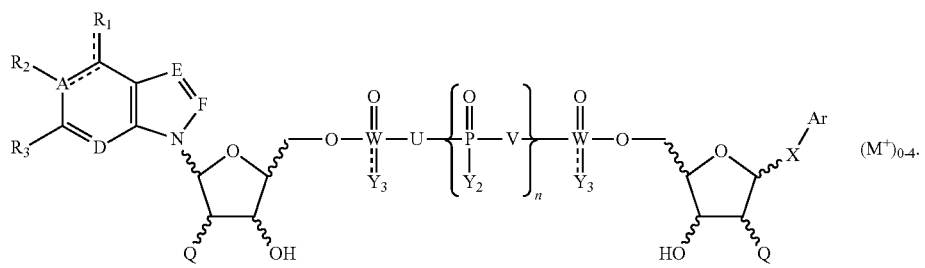

(IIA-1)

4. The compound of claim 2, which is a compound of formula IIA-2:

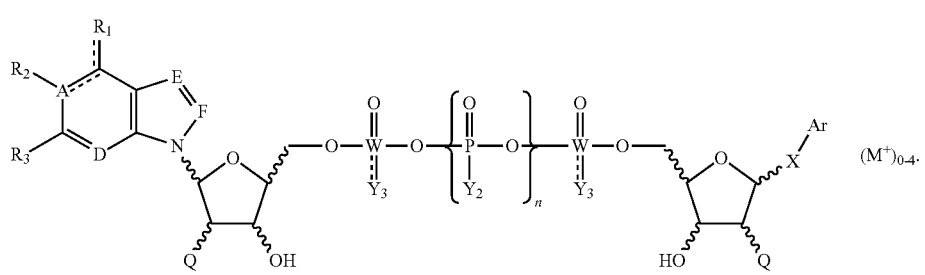

(IIA-2)

5. A compound of Formula IIB:

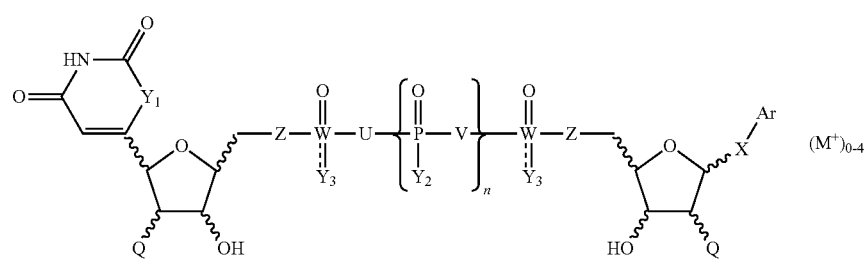

(IIB)

or enantiomers, diastereomers, enantiomerically enriched mixtures, racemic mixtures, crystalline forms, non-crystalline forms, amorphous forms, or pharmaceutically acceptable salts thereof, wherein:

Ar is an aryl, alkyl, cycloalkyl, arylalkyl, or a heteroaryl or fused heteroaryl group containing 1-4 heteroatoms; each of which is optionally substituted with one or more of a halo, hydroxy, alkyl, alkoxy, carboxy, cyano, nitro, sulfonamido, sulfonate, amino, alkylamino, or di-alkylamino group or groups; provided that when X is O, Ar is neither unsubstituted phenyl, anilino, nor 4-nitrophenyl;

X is a bond or is selected from the group consisting of O, S, S(O), S(O$_2$), N(R'), —C(O)N(R')—, and —(CH$_2$)$_m$X$^1$—;

X$^1$ is O, S, S(O), S(O$_2$), or N(R');

R' is H, alkyl, or aralkyl;

Q represents independently for each occurrence an H; OH; lower alkoxy; halo; mono-, di- or trihalomethyl; amino; lower alkylamino; or lower dialkylamino group;

U and V each represent independently for each occurrence O; NH; a lower alkylamino diradical; a lower dialkylamino diradical; methylene; or mono- or dihalomethylene;

Y$_1$ is CH$_2$ or NH;

Y$_2$ and Y$_3$ each represent independently for each occurrence O, O$^-$; S$^-$; or a substituted or unsubstituted lower alkoxy, aryloxy, aralkyloxy, or cycloalkyloxy group;

M is H or a salt-forming cation;

Z represents independently for each occurrence O, NH, or a lower alkylamino diradical;

m and n are independently 0, 1 or 2;

W is P.

6. A compound of Formula IV:

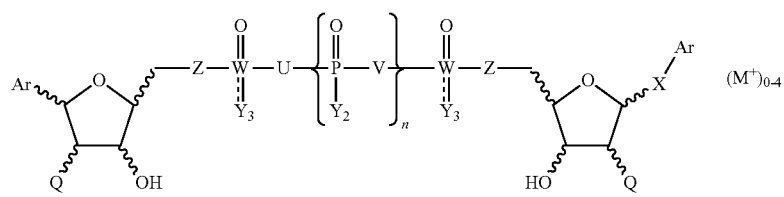

(IV)

or enantiomers, diastereomers, enantiomerically enriched mixtures, racemic mixtures, crystalline forms, non-crystalline forms, amorphous forms, or pharmaceutically acceptable salts thereof, wherein:

Ar is an aryl, alkyl, cycloalkyl, aralkyl, or a heteroaryl or fused heteroaryl group containing 1-4 heteroatoms; each of which is optionally substituted with one or more of a halo, hydroxy, alkyl, alkoxy, carboxy, cyano, nitro, sulfonamido, sulfonate, amino, alkylamino, or di-alkylamino group or groups; provided that when X is O, Ar is neither unsubstituted phenyl, anilino, nor 4-nitrophenyl;

X is O, S, S(O), S(O$_2$), N(R'), —C(O)N(R')—, or —(CH$_2$)$_m$X$^1$—;

X$^1$ is O, S, S(O), S(O$_2$), or N(R');

R' is H, alkyl, or aralkyl;

Q represents independently for each occurrence an H; OH; lower alkoxy; halo; mono-, di- or trihalomethyl; amino; lower alkylamino; or lower dialkylamino group;

U and V each represent independently for each occurrence O; NH; a lower alkylamino diradical; a lower dialkylamino diradical; methylene; or mono- or dihalomethylene;

Y$_2$ and Y$_3$ each represent independently for each occurrence O, O$^-$; S$^-$; or a substituted or unsubstituted lower alkoxy, aryloxy, aralkyloxy, or cycloalkyloxy group;

M is H or a salt-forming cation;

Z represents independently for each occurrence O, NH, or a lower alkylamino diradical;

m and n are independently 0, 1 or 2; and

W is P.

7. A method of treating constipation or chronic idiopathic constipation comprising administering to a subject in need thereof a therapeutically effective amount of a compound of claim 1.

8. The method of claim 7 wherein the subject is a human.

9. A method of treating constipation or chronic idiopathic constipation comprising administering to a subject in need thereof a therapeutically effective amount of a compound of claim 2.

10. The method of claim 9 wherein the subject is a human.

11. A method of treating constipation or chronic idiopathic constipation comprising administering to a subject in need thereof a therapeutically effective amount of a compound of claim 3.

12. The method of claim 11 wherein the subject is a human.

13. A method of treating constipation or chronic idiopathic constipation comprising administering to a subject in need thereof a therapeutically effective amount of a compound of claim 5.

14. The method of claim 13 wherein the subject is a human.

15. A method of treating constipation or chronic idiopathic constipation comprising administering to a subject in need thereof a therapeutically effective amount of a compound of claim 6.

16. The method of claim 15 wherein the subject is a human.

* * * * *